(12) United States Patent
Shulepov et al.

(10) Patent No.: US 11,400,487 B2
(45) Date of Patent: Aug. 2, 2022

(54) BROADBAND ULTRASOUND TRANSDUCER

(71) Applicant: KONINKLIJKE PHILIPS N.V., Eindhoven (NL)

(72) Inventors: Sergei Shulepov, Eindhoven (NL); Petrus Henricus Maria Timmermans, Teteringen (NL); Peter Dirksen, Hilversum (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 375 days.

(21) Appl. No.: 16/309,170

(22) PCT Filed: Jun. 13, 2017

(86) PCT No.: PCT/EP2017/064363
§ 371 (c)(1),
(2) Date: Dec. 12, 2018

(87) PCT Pub. No.: WO2017/216139
PCT Pub. Date: Dec. 21, 2017

(65) Prior Publication Data
US 2019/0176193 A1 Jun. 13, 2019

(30) Foreign Application Priority Data
Jun. 13, 2016 (EP) .................................. 16174192

(51) Int. Cl.
*B06B 1/02* (2006.01)
*A61B 8/00* (2006.01)
(Continued)

(52) U.S. Cl.
CPC .......... *B06B 1/0292* (2013.01); *A61B 8/4483* (2013.01); *G01N 29/22* (2013.01); *G01N 29/2406* (2013.01); *G01S 15/8925* (2013.01)

(58) Field of Classification Search
CPC .. B06B 1/0292; G01N 29/22; G01N 29/2406; G01S 15/8925; A61B 8/4483
See application file for complete search history.

(56) References Cited

U.S. PATENT DOCUMENTS

| 8,869,622 B2 | 10/2014 | Fujii | |
|---|---|---|---|
| 2005/0015009 A1* | 1/2005 | Mourad | A61B 5/7267 600/438 |

(Continued)

FOREIGN PATENT DOCUMENTS

| GB | 2459866 A | 11/2009 |
|---|---|---|
| JP | 2014023775 A | 2/2014 |

(Continued)

OTHER PUBLICATIONS

Wong, et al., "Capacitive Micromachined Ultrasonic Transducers for High Intensity Focused Ablation of Upper Abdominal Tumors", 2006 IEEE Ultrasonics Symposium, Oct. 1, 2006, pp. 841-844.

*Primary Examiner* — Hien N Nguyen

(57) ABSTRACT

A transducer array (10) is disclosed comprising a plurality of CMUT cells (100, 100, 100"), each CMUT cell comprising a first electrode (110) supported by a substrate (101) and a second electrode (120) supported by a membrane suspended over a cavity (105) between the first electrode and the second electrode, the plurality of CMUT cells comprising a first group of CMUT cells (100) each having a membrane comprising a first layer stack (130); and a second group of CMUT cells (100') each having membrane comprising a second layer stack (130'), the second layer stack including a layer (135) of a material having a higher density than any of the layers in the first layer stack. Also disclosed is a device comprising such a transducer array, an ultrasound imaging system including such a transducer array and a method of operating such an ultrasound imaging system.

14 Claims, 14 Drawing Sheets

(51) Int. Cl.
*G01N 29/24* (2006.01)
*G01S 15/89* (2006.01)
*G01N 29/22* (2006.01)

(56) References Cited

U.S. PATENT DOCUMENTS

2007/0215964 A1 9/2007 Khuri-Yakub et al.
2014/0265720 A1 9/2014 El-Gamal et al.
2015/0013462 A1 1/2015 Takenaka et al.

FOREIGN PATENT DOCUMENTS

| WO | 02090242 A1 | 11/2002 |
| WO | 2013093728 A1 | 6/2013 |
| WO | 2015028945 A2 | 3/2015 |
| WO | 2016008833 A1 | 1/2016 |

\* cited by examiner

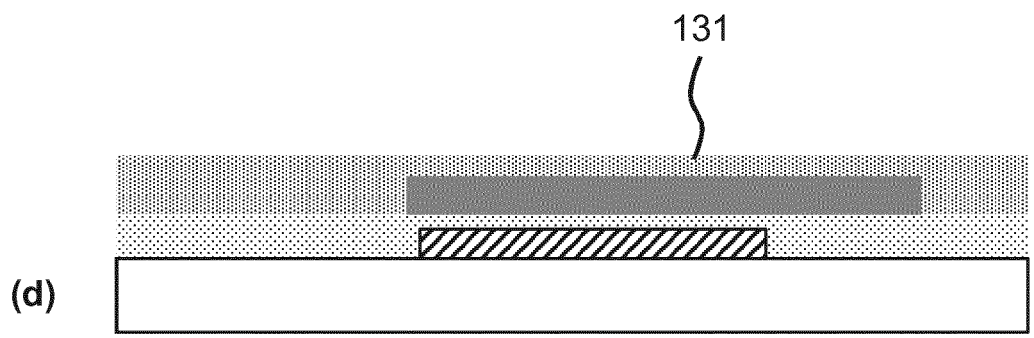
(d)
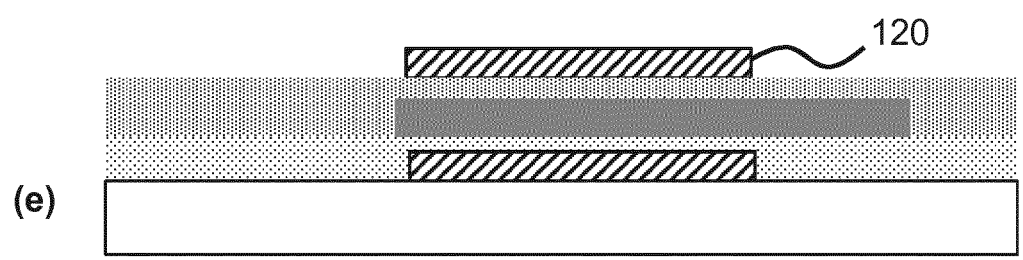
(e)
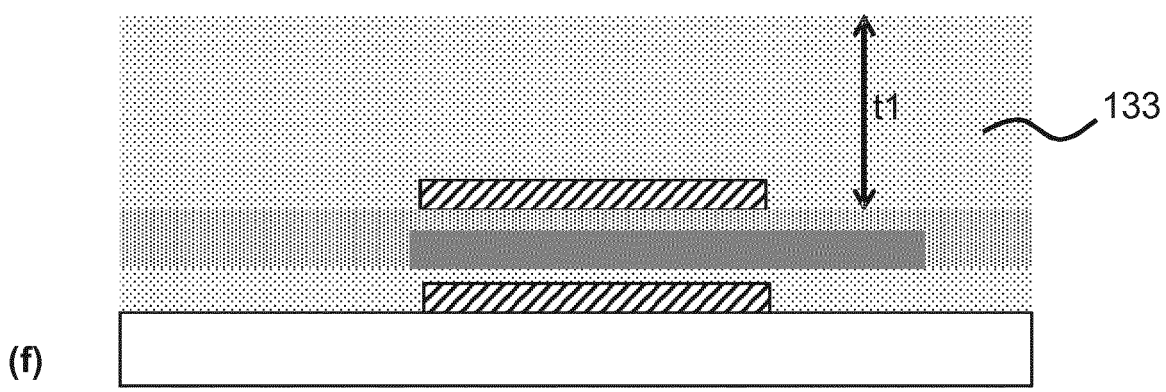
(f)
FIG. 8 (continued)

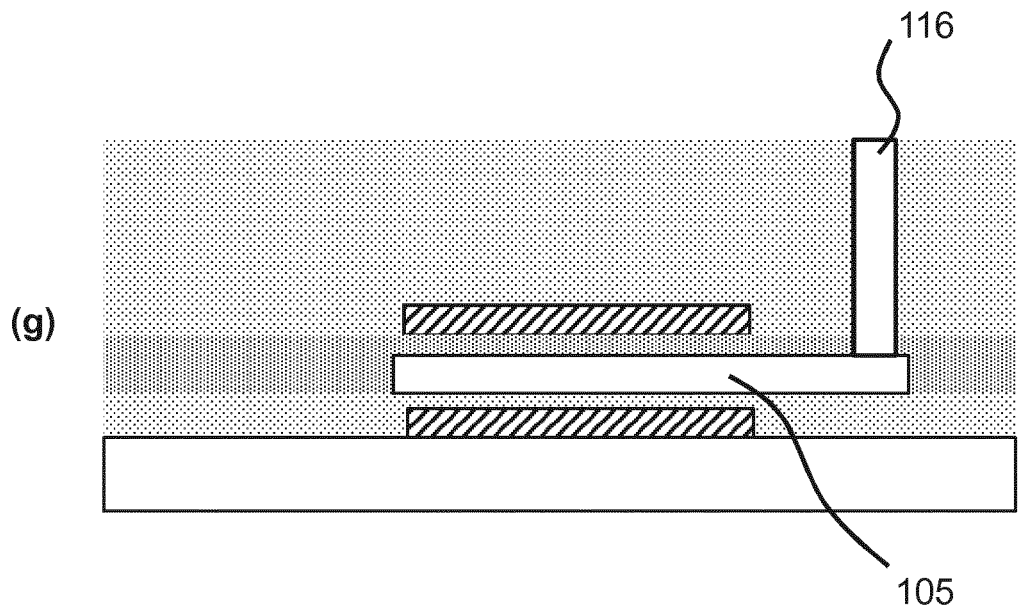
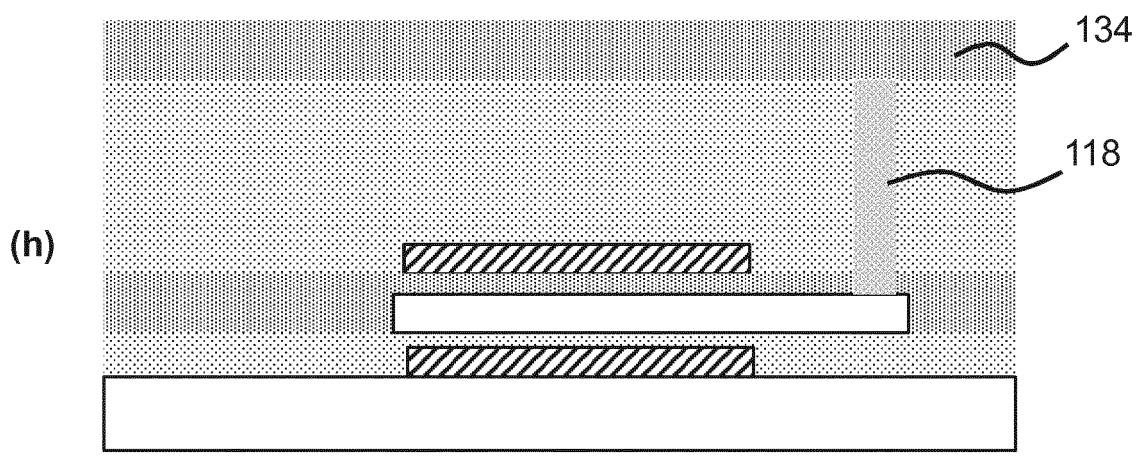
FIG. 8 (continued)

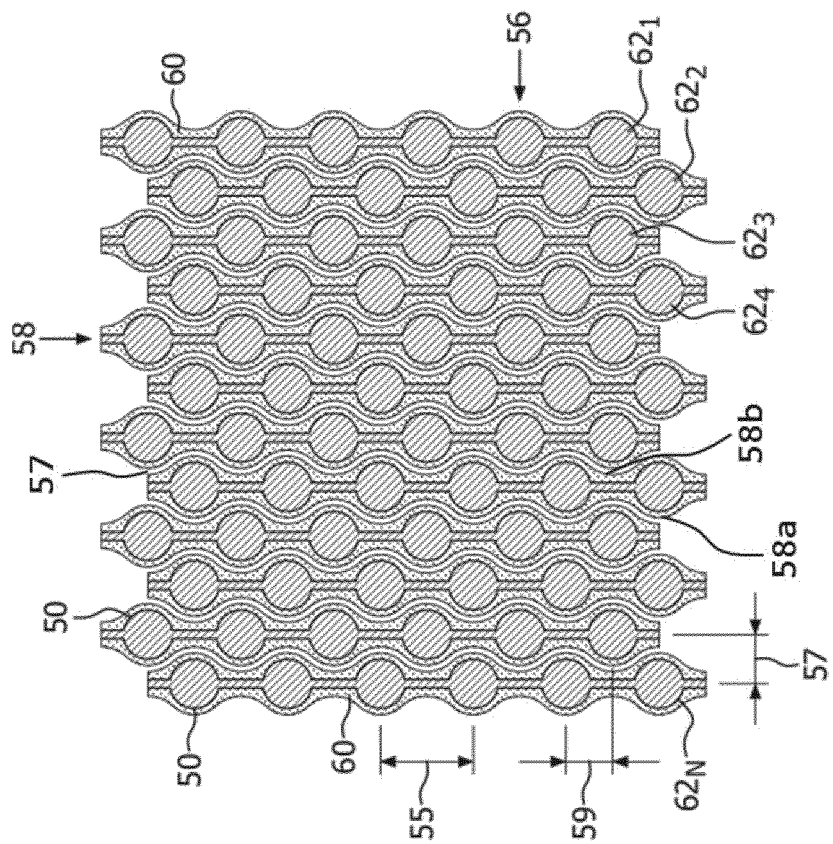
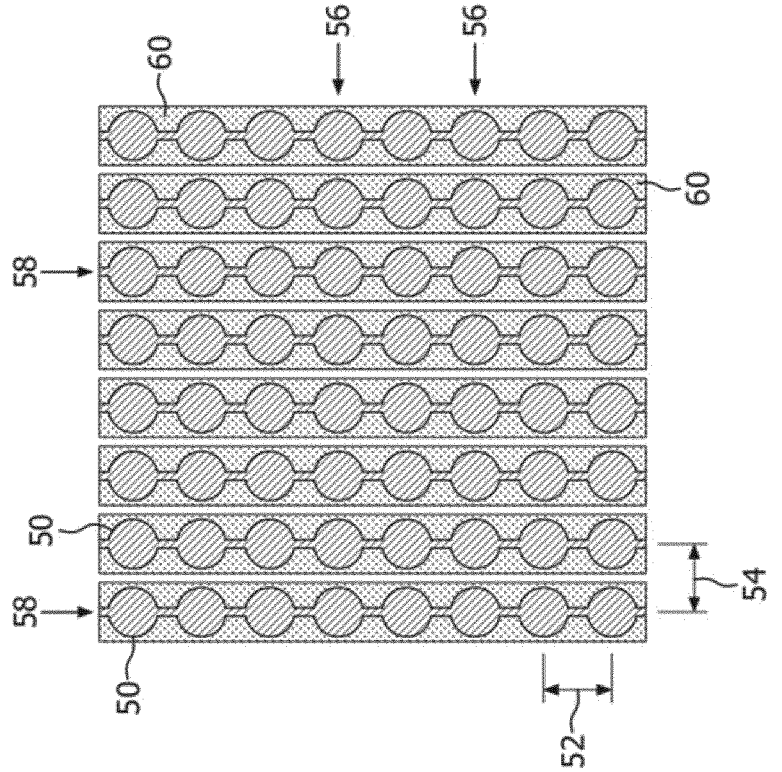

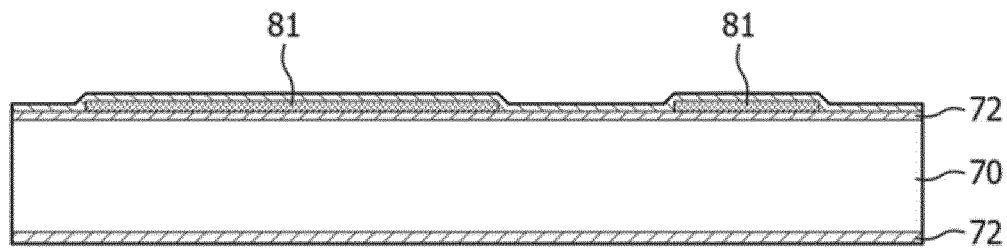
(a)
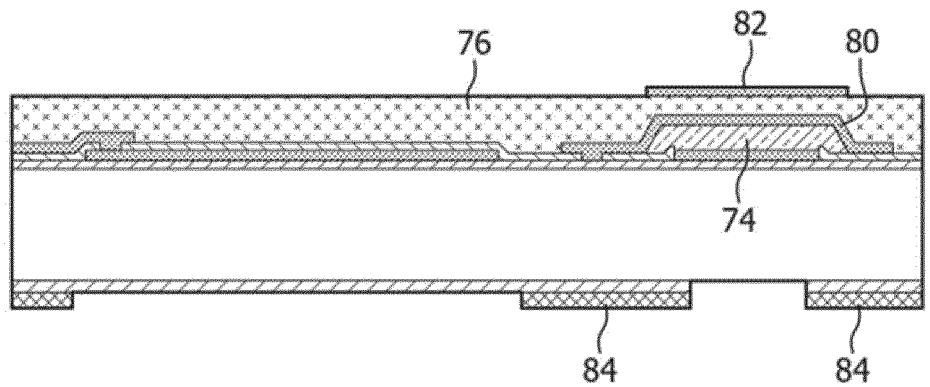
(b)
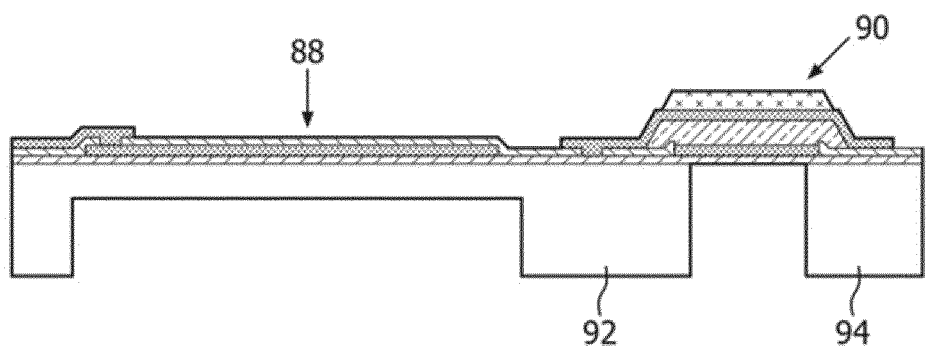
(c)
FIG. 11

250

BROADBAND ULTRASOUND TRANSDUCER

This application is the U.S. National Phase application under 35 U.S.C. § 371 of International Application No. PCT/EP2017/064363, filed on Jun. 13, 2017, which claims the benefit of European Application Serial No. 16174192.1, filed Jun. 13, 2016. These applications are hereby incorporated by reference herein.

FIELD OF THE INVENTION

The present invention relates to a transducer array comprising a plurality of CMUT cells, each CMUT cell comprising a first electrode supported by a substrate and a second electrode supported by a membrane suspended over a cavity between the first electrode and the second electrode, the plurality of CMUT cells comprising a first group of CMUT cells and a second group of CMUT cells different to the first group of CMUT cells.

The present invention further relates to a device comprising such a transducer array.

The present invention still further relates to an ultrasound imaging system comprising such a transducer array.

The present invention still further relates to a method of operating such an ultrasound imaging system.

BACKGROUND OF THE INVENTION

Ultrasonic transducers used for medical imaging have numerous characteristics that lead to the production of high quality diagnostic images. Among these are broad bandwidth, affecting resolution and high sensitivity, which combined with pressure output affects depth of field, to low level acoustic signals at ultrasonic frequencies. Conventionally the piezoelectric materials which possess these characteristics have been made of PZT and PVDF materials, with PZT being particularly popular as the material of choice. However, PZT suffers from a number of notable drawbacks. Firstly, the ceramic PZT materials require manufacturing processes including dicing, matching layer bonding, fillers, electroplating and interconnections that are distinctly different and complex and require extensive handling, all of which can result in transducer stack unit yields that are lower than desired. This manufacturing complexity increases the cost of the final transducer probe and puts design limitations on the minimum spacing between the elements as well as the size of the individual elements. Moreover, PZT materials have a poorly matched impedance to water or biological tissue, such that matching layers need to be added to the PZT materials in order to obtain the desired acoustic impedance matching with the medium of interest.

As ultrasound system mainframes have become smaller and dominated by field programmable gate arrays (FPGAs) and software for much of the signal processing functionality, the cost of system mainframes has dropped with the size of the systems. Ultrasound systems are now available in inexpensive portable, desktop and handheld form, for instance for use as ultrasound diagnostic imaging systems or as ultrasound therapeutic systems in which a particular (tissue) anomaly is ablated using high-energy ultrasound pulses. As a result, the cost of the transducer probe is an ever-increasing percentage of the overall cost of the system, an increase which has been accelerated by the advent of higher element-count arrays used for 3D imaging in the case of ultrasound diagnostic imaging systems. The probes used for ultrasound 3D imaging with electronic steering rely on specialized semiconductor devices application-specific integrated circuits (ASICs) which perform microbeam forming for two-dimensional (2D) arrays of transducer elements. Accordingly it is desirable to be able to manufacture transducer arrays with improved yields and at lower cost to facilitate the need for low-cost ultrasound systems, and preferably by manufacturing processes compatible with semiconductor production.

Recent developments have led to the prospect that medical ultrasound transducers can be batch manufactured by semiconductor processes. Desirably these processes should be the same ones used to produce the ASIC circuitry needed by an ultrasound probe such as a CMOS process. These developments have produced micromachined ultrasonic transducers or MUTs, the preferred form being the capacitive MUT (CMUT). CMUT transducers are tiny diaphragm-like devices with electrodes that convert the sound vibration of a received ultrasound signal into a modulated capacitance. For transmission the capacitive charge applied to the electrodes is modulated to vibrate/move the diaphragm of the device and thereby transmit an ultrasound wave. Since these diaphragms are manufactured by semiconductor processes the devices generally have dimensions in the 10-500 micrometer range, with spacing between the individual diaphragms less than a few micrometers. Many such individual CMUTs can be connected together and operated in unison as a single transducer element. For example, four to sixteen CMUTs can be coupled together to function in unison as a single transducer element. A typical 2D transducer array can have 2000-3000 CMUT transducer elements.

The manufacture of CMUT transducer-based ultrasound systems is therefore more cost-effective compared to PZT-based systems. Moreover, due to the materials used in such semiconductor processes, the CMUT transducers exhibit much improved acoustic impedance matching to water and biological tissue, which obviates the need for a matching layer and yields an improved effective bandwidth.

One of the main challenges in developing effective ultrasound systems, and in particular CMUT transducer-based ultrasound systems is to provide systems with excellent image resolution and good depth-of-field in case of an ultrasound diagnostic imaging system. These are conflicting requirements, as higher frequency pulsed ultrasound leads to improved resolution but shorter depth-of-field due to the frequency dependent attenuation of the medium. In order to obtain high resolution in depth, high pressure short pulses are desired which require a large bandwidth. Although in principle CMUT transducers can generate a broad spectrum of frequencies the bandwidth is limited because the frequency at which they operate efficiently depends strongly on the applied static bias voltage over the CMUT. Efforts have been made to increase the operational bandwidth of CMUT-based ultrasound transducer arrays by differentiating the CMUT cells within the array such that the array comprises groups of CMUT cells with different spring constants. For example, U.S. Pat. No. 5,870,351 discloses a broadband micro-fabricated ultrasonic transducer which includes a plurality of resonant membranes of different sizes (diameters) and/or shapes to broaden the frequency response of the ultrasonic transducer.

US 2014/0010388 A1 discloses a capacitive transducer having broadband frequency characteristics. The capacitive transducer includes an element which has multiple kinds of cells, each cell including: a first electrode; a vibrating film including a second electrode, the second electrode being opposed to the first electrode with a gap; and a support portion that supports the vibrating film so as to form the gap.

The multiple kinds of cells have different ratios of an area of one of the first electrode and the second electrode to an area of the gap when viewed from a normal direction of the vibrating film. In addition, the spring constant of some of the cells may be altered by an additional layer on the vibrating films (membranes) of the cells.

As is well-known per se, the acoustic power (output pressure) produced by the CMUT cells may be optimized by operating the CMUT cells in so-called collapse mode in which the CMUT cells are driven by a bias voltage that drives a central part of the diaphragm or flexible membrane across the gap onto the opposing substrate and provided with a stimulus having a set frequency that causes the diaphragm or flexible membrane to resonate at the set frequency. This is for instance demonstrated by K. K. Park et al. in "Comparison of conventional and collapse-mode CMUT in 1-D array configuration", as retrieved from the Internet on 9 Jun. 2015 from URL: http://www-kyg.stanford.edu/khuriyakub/opencms/Downloads/11_Park_02.pdf.

However, in order to safeguard the lifetime of the CMUT cells, it is imperative that the central regions of the cells are kept in contact with the opposing substrate. As the bias voltage at which the CMUT cells collapse onto the opposing substrate is directly proportional to the spring constant of the cells, it is undesirable to have CMUT cells with significantly different spring constants within the transducer array, as this can cause some of the CMUT cells to temporarily release from the opposing substrate in collapse mode when a single bias voltage is applied to all CMUT cells, which increases the risk of premature cell failure, as previously explained.

SUMMARY OF THE INVENTION

The present invention seeks to provide a transducer array comprising a plurality of CMUT cells that combines broadband characteristics and an excellent lifetime when operated in collapse mode.

The present invention further seeks to provide a device comprising such a transducer array.

The present invention further seeks to provide an ultrasound imaging system comprising such a device and/or transducer array.

The present invention further seeks to provide a method of operating such an ultrasound imaging system.

According to an aspect, there is provided a transducer array comprising a plurality of CMUT cells, each CMUT cell comprising a first electrode supported by a substrate and a second electrode supported by a membrane suspended over a cavity between the first electrode and the second electrode, the plurality of CMUT cells comprising a first group of CMUT cells each having a membrane comprising a first layer stack; and a second group of CMUT cells each having membrane comprising a second layer stack, the second layer stack including a layer of a material having a higher density than any of the layers in the first layer stack, wherein the membranes of the first group of CMUT cells have a first spring constant and the membranes of the second group of CMUT cells have a second spring constant that is no more than 20% different to the first spring constant. The present invention is based on the insight that the provision of a (thin) layer of a high density material to selected CMUT cells in order to differentiate the CMUT cells of the transducer array may be used to significantly increase the mass of the membranes of the selected CMUT cells without significantly increasing the spring constant of these membranes. Consequently, CMUT cells of the transducer array may still collapse at approximately the same bias voltage yet exhibit different resonance frequencies due to the difference in mass of the membranes of the first group and second group of CMUT cells respectively, thereby yielding a transducer array that can be safely operated in collapse mode and that exhibits an increased bandwidth, i.e. broadband characteristics, compared to CMUT transducer arrays in which all CMUT cells have the same geometry. For this reason, the material preferably also has a lower Young's modulus compared to the material of any of the layers of the first layer stack, such that the high density material has a minimal contribution to the overall bending stiffness of the membranes of the second group of CMUT cells. For example, the material having a higher density than any of the layers in the first layer stack may have a density in excess of 7 g/cm$^3$, preferably a density in excess of 10 g/cm$^3$ and a Young's modulus of less than 200 GPa, preferably a Young's modulus of less than 100 GPa.

Preferably, the second spring constant is no more than 10% different to the first spring constant to ensure that all CMUT cells of the transducer array enter collapse mode at approximately the same bias voltage. In some embodiments, the spring constant of the membranes of the first group of CMUT cells is the same as the spring constant of the membranes of the second group of CMUT cells. The tuning of the spring constant of the respective membranes may be achieved by selecting the materials and tuning the thickness of the layers of these materials in the membranes of the first group and second group of CMUT cells respectively.

For example, the first layer stack may comprise a layer of a dielectric material to a first thickness; and the second layer stack may comprise a layer of the dielectric material to a second thickness that is smaller than the first thickness. The second thickness may be chosen such that the combination of the dielectric material layer to the second thickness in the second layer stack and the thickness of the layer of the material having a higher density than any of the layers in the first layer stack provides (approximately) the same contribution to the overall spring constant of the membranes of the CMUT cells in the second group as the layer of the dielectric material to the first thickness achieves for the membranes of the CMUT cells in the first group.

Alternatively, the second layer stack may be the same as the first layer stack apart for the layer of the material having a higher density than any of the layers in the first layer stack being an additional layer. This provides an ultrasound transducer array that may be manufactured in a particularly straightforward manner, e.g. by the selective deposition of the layer of the high density material to the CMUT cells of the second group.

The transducer array may comprise a plurality of transducer elements, wherein each transducer element comprises at least one CMUT cell of the first group and at least one CMUT cell of the second group.

In an embodiment, the CMUT cells of the first group each have a first diameter and the CMUT cells of the second group each have a second diameter that is different to the first diameter. In collapse mode, the resonance frequency of the CMUT cells becomes largely independent of cell diameter, such that the addition of the high density material layer to the second group of CMUT cells introduces an alternative design freedom to achieve broadband characteristics in an ultrasound transducer array operable in collapse mode having CMUT cells of different diameters.

The layer of a material having a higher density than any of the layers in the first layer stack may be a continuous layer or may be a patterned layer. Patterning the layer may be used to further tune the mass of the membranes of the CMUT cells to which the layer is applied. For example, the second group of CMUT cells may comprise a first sub group in which the membranes of the CMUT cells comprise a continuous layer of the high density material and a second sub group in which the membranes of the CMUT cells comprise a patterned layer of the high density material. In this manner, the frequency characteristics of the ultrasound transducer array may be tuned in a more fine-grained manner.

In an embodiment, the layer of a material having a higher density than any of the layers in the first layer stack is a metal layer, preferably a gold layer or a platinum layer. Metals may be used due to their high density, which makes these materials particular suitable for use as a high density material layer. In the context of the present application, the term metal also includes metal alloys.

In a particularly advantageous embodiment, the CMUT cells or transducer elements are arranged in a staggered array comprising a first column of spaced CMUT cells or transducer elements on at least one silicon island; a second column of spaced CMUT cells or transducer elements on at least one further silicon island, the second column being staggered in alignment with the first column such that cells of the second column are partially located in spaces between successive cells of the first column, the first column and the second column being spaced apart by a gap; and a flexible foil retaining the respective silicon islands, the flexible foil comprising conductive interconnects.

By staggering such columns, the cells or transducer elements of one column can be interspersed among the cells or transducer elements of an adjacent column, providing a smaller array pitch in both the steered direction without necessarily increasing the pitch in the unsteered direction. To be able to bend the array for curved array and catheter applications the elements of the array are fabricated on silicon islands of as few as one or several cells or transducer elements per island, and the island are joined by an integral flexible foil overlay that facilitates a continuous sideways looking array of CMUT cells or transducer elements to be fully wrapped around a 3-dimensional body, e.g. a cylindrical body such as a catheter sheath without discontinuities between array domains. This therefore facilitates the generation of ultrasound images with improved image quality and reduced image artefacts such as grating lobes due to the reduced pitch between CMUT cells or transducer elements. The first group of CMUT cells and the second group of CMUT cells or the transducer elements preferably are each arranged at a constant pitch in the staggered array to optimize performance of the transducer array.

In an embodiment, the first column of spaced CMUT cells or transducer elements is located on a first silicon island having opposing meandering edges, each edge meandering outwardly around one of the CMUT cells or transducer elements and meandering inwardly into a space between the CMUT cells or transducer elements; the second column of spaced CMUT cells or transducer elements is located on a second silicon island having opposing meandering edges, each edge meandering outwardly around one of the CMUT cells or transducer elements and meandering inwardly into a space between the CMUT cells or transducer elements; and the first silicon island is arranged adjacent to the second silicon island such that an outwardly meandering edge portion of the first silicon island slots into an inwardly meandering edge portion of the second silicon island. Such an array benefits from the structural integrity provided by each silicon island carrying a plurality (i.e. a column) of CMUT cells or transducer elements, with the shape of the silicon islands facilitating a particular dense packing of the silicon islands to yield the staggered array of CMUT cells or transducer elements. In addition, due to the fact that the silicon islands may be arranged along the length of a catheter, the resulting transducer array combines good structural integrity with excellent flexibility of the array.

The first silicon island and the second silicon island each may comprise at least a pair of said columns of spaced CMUT cells or transducer elements, wherein the columns in said pair are staggered. This limits the number of separate silicon islands in the array whilst still providing excellent flexibility of the array due to the limited width of the respective silicon islands.

Such a silicon-island based embodiment of the ultrasound transducer array may, in a further aspect, form part of a catheter comprising an external sheath, with the CMUT transducer array wrapped around the external sheath such that the respective columns of the array extend in a length direction of the catheter. Such a catheter benefits from improved imaging capability due to the continuous nature of the CMUT transducer array wrapped around its external sheath.

The catheter may additionally comprise a further CMUT transducer array at a distal end of the catheter, e.g. at the distal tip of the catheter, to further enhance the imaging capability of the catheter. Such a catheter for instance may be able to generate look-ahead images with the further CMUT transducer array as well as 360° images with the CMUT transducer array.

In some embodiments, the catheter may be an intracardiac or an intravascular catheter.

In alternative embodiments, the transducer array may form part of a device which further includes a controller configured to control the CMUT transducer array. The device may, for instance, include a probe comprising the CMUT transducer array. The probe may, for example, be a needle-like probe, a TEE (transesophageal echocardiography)-probe or a diagnostic ultrasound probe.

According to a further aspect, there is provided an ultrasound imaging system comprising a patient interface module and the transducer array or the catheter according to any of the described embodiments of the present invention. Such an ultrasound imaging system benefits from the improved broadband characteristics of the ultrasound transducer array as provided by the differentiated CMUT cells of the array.

The ultrasound imaging system preferably further comprises a power supply adapted to operate the CMUT cells in a collapse mode during at least one of an ultrasound transmission mode and an ultrasound reception mode. The ultrasound transducer array is particularly suitable for such collapse mode operation due to the comparable spring constants (bending stiffness) of the respective CMUT cell membranes within the ultrasound transducer array as explained above.

According to yet another aspect, there is provided a method of operating such an ultrasound imaging system, the method comprising applying, during an ultrasound transmission mode of the ultrasound imaging system, a control signal to the CMUT cells, the control signal comprising a DC component forcing the CMUT cells into a collapse mode and an AC component forcing the collapsed CMUT cells to resonate, wherein the CMUT cells of the first group and the CMUT cells of the second group resonate at different resonance frequencies. This operating method ensures that the ultrasound imaging system achieves broadband characteristics in collapse mode without significantly compromising the lifetime of the array.

BRIEF DESCRIPTION OF THE DRAWINGS

Embodiments of the invention are described in more detail and by way of non-limiting examples with reference to the accompanying drawings, wherein:

FIG. 9 is a plan view of a symmetrically arranged CMUT array of rows and columns of CMUT cells according to an embodiment;

FIG. 10 is a plan view of a CMUT array configured with staggered rows of cells with the cells of adjacent rows and columns interspersed within each other according to another embodiment;

FIG. 11 illustrates steps in the fabrication of a flexible interconnect of adjacent cell silicon islands according to an embodiment;

DETAILED DESCRIPTION OF THE EMBODIMENTS

Figure 1:
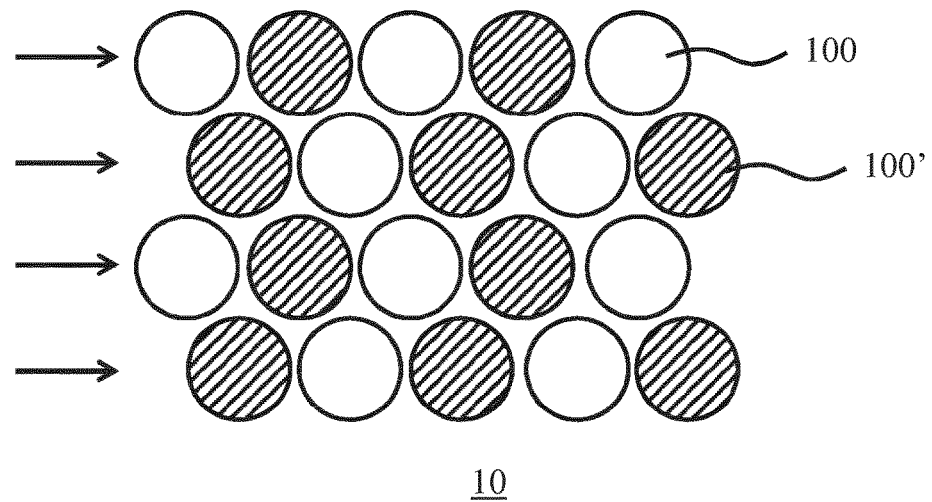
FIG. 1 schematically depicts a top view of an ultrasound transducer array according to an embodiment.

It should be understood that the Figures are merely schematic and are not drawn to scale. It should also be understood that the same reference numerals are used throughout the Figures to indicate the same or similar parts.

In the context of the present application, where reference is made to a membrane, this is a deformable structure that spans the gap or cavity over the substrate of a capacitive micromachined ultrasound transducer (CMUT), and that supports, e.g. embeds one of the electrodes of the CMUT, e.g. an electrode opposing a further electrode on the substrate and separated therefrom by a gap or cavity.

In the context of the present application, where reference is made to a membrane layer stack, this is intended to include membranes formed of a single layer as well as membranes formed of multiple layers, but excluding the electrode embedded in or otherwise supported by the membrane.

In the context of the present application, where reference is made to a CMUT element or transducer element, this may equate to a single CMUT cell or to a cluster of CMUT cells arranged to be operated in unison, e.g. arranged to be addressed by a single control signal.

Figure 2:
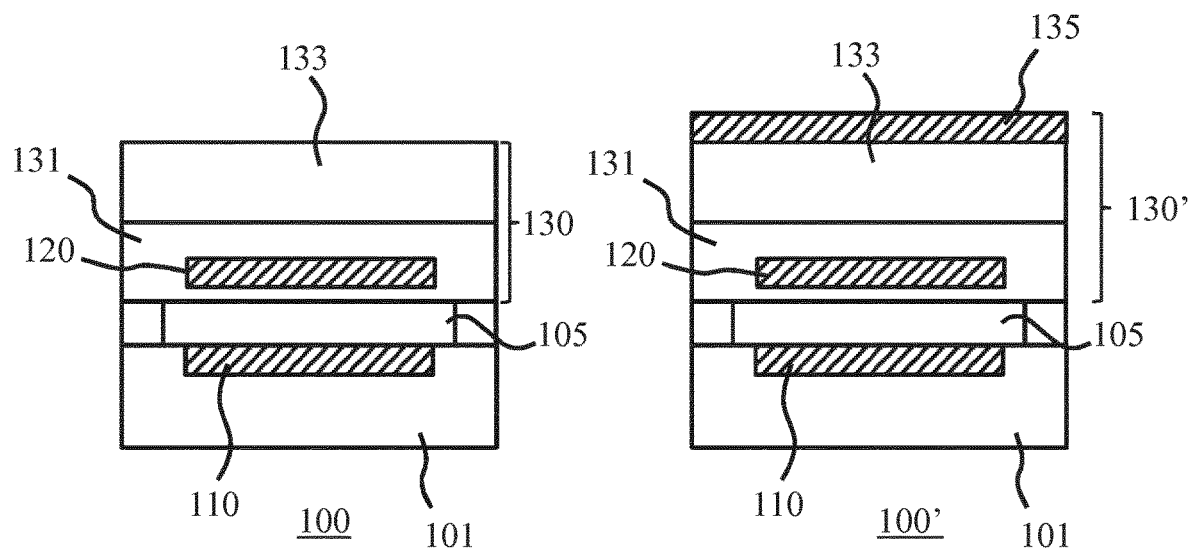
FIG. 2 schematically depicts a cross-section of an ultrasound transducer array according to an embodiment.

FIG. 1 schematically depicts a top view of an ultrasound transducer array 10 according to an embodiment. The ultrasound transducer array 10 comprises a plurality of CMUT cells, which are divided in a first group of CMUT cells 100 and a second group of CMUT cells 100', here shown to have a circular shape by way of non-limiting example only. Other shapes may be contemplated for the CMUT cells 100, 100'. The cells 100, 100' may be arranged to be addressed individually although preferably clusters of cells are addressable in unison, i.e. as a transducer element, with a cluster comprising both cells 100, 100', preferably an equal number of cells 100, 100' such that each transducer element exhibits the same broadband characteristics, which will be explained in more detail below. The ultrasound transducer array 10 may be an array of such transducer elements. The CMUT cells 100, 100' may be arranged in a staggered fashion as shown in FIG. 1 to increase the cell density of the ultrasound transducer array 10. Cells 100, 100' in a single row may be clustered, e.g. addressed by a single row address signal, as indicated by the horizontal arrows. FIG. 2 schematically depicts a cross-section of a CMUT cell 100 of the first group and a CMUT cell 100' of the second group respectively. Each CMUT cell comprises a first electrode 110 supported by a substrate 101 and a second electrode 120 opposing the first electrode 110 and separated therefrom by a cavity 105.

In the first group of CMUT cells 100, the second electrode 120 is supported by a flexible membrane comprising a first layer stack 130, which for example includes a first layer 131 and a second layer 133 of an electrically insulating or dielectric material such as silicon oxide, silicon nitride and so on. In some applications, e.g. low-frequency applications, the first layer stack 130 may have a thickness well in excess of 1 micron, e.g. a thickness in the range of 5-20 microns. In some other applications, e.g. high-frequency applications, the first layer stack 130 may have a thickness of less than 2 microns. The second electrode 120 may be embedded in the flexible membrane comprising the first layer stack 130 such that the second electrode 120 is separated from the cavity 105 by a thin layer of dielectric material, for example to prevent a short circuit between the first electrode 110 and the second electrode 120 upon a central region of the flexible membrane contacting the substrate 101, e.g. during operation of the CMUT cells 100, 100' of the ultrasound transducer array 10 in collapse mode.

In the second group of CMUT cells 100', the second electrode 120 is supported by a flexible membrane comprising a second layer stack 130', which includes a layer 135 of a material having a higher density than any of the layers in the first layer stack 130. The layer 135 will be referred to as the mass layer 135 in the remainder of this description. The mass layer 135 is present in the membrane layer stack 130' of the second group of CMUT cells 100' to increase the mass of the membrane layer stack 130' without significantly affecting its bending stiffness, which bending stiffness largely defines the spring constant of the CMUT cells 100, 100', in particular when the CMUT cells 100, 100' are operated in a collapse mode in which a central part of the membranes is permanently collapsed onto the substrate 101, with the peripheral portion of the membranes around the central portion oscillating to generate an ultrasound pulse having a desired frequency spectrum in a transmission mode of the ultrasound transducer 10 or resonating in response to a pulse echo having a desired frequency spectrum being received in a reception mode of the ultrasound transducer 10. As such collapse mode operation is well-known per se, this will not be explained in further detail for the sake of brevity only.

The center frequency $F_c$ of a circular CMUT cell membrane may be approximated by the following equation (1):

$$F_c \approx \frac{2}{R^2}\sqrt{\frac{D}{\rho \cdot t}}\frac{1}{(1-x^2)}$$

In this equation, R is the membrane radius, p is the membrane density, D is the flexural rigidity (spring constant) of the membrane, t is the membrane thickness and x is the ratio $R_c/R$ wherein $R_c$ is the radius of the central portion of the membrane collapsed onto the substrate 101 ($R_c=0$ when the membrane is not in collapse). As can be derived from this equation, the resonance frequency of the membrane depends on both the flexural rigidity (spring constant) D and the density p of the membrane. However, the energy or force required to collapse the membrane onto the substrate 101, e.g. to force the CMUT cell into collapse mode, is dominated by the flexural rigidity D of the membrane. Therefore, embodiments of the present invention are directed to increasing the mass of the layer stack 130' of the second group of CMUT cells 100' compared to the mass of the layer stack 130 of the first group of CMUT cells 100 whilst minimizing the difference in spring constants between the membranes comprising the first layer stack 130 and the second layer stack 130' respectively.

The flexural rigidity D of the membrane may be expressed by the effective Young's modulus $E_{eff}$ of the membrane layer stack (equation (2)):

$$D = \frac{E_{eff} \cdot t^3}{12(1-\mu^2)}$$

In this equation, μ is the Poisson ratio. The effect of the addition of a mass layer 135 to the effective Young's modulus may be -approximated by the following equation (3):

$$E_{eff} \approx \frac{E_1 * t_1 + E_2 * t_2}{(t_1 + t_2)}$$

In this equation, $E_1$ and $t_1$ are the Young's modulus and thickness respectively of the membrane stack and $E_2$ and $t_2$ are the Young's modulus and thickness respectively of the mass layer 135. For example, for a (multi-layer) silicon nitride membrane stack having a thickness of 3 microns and a gold mass layer having a thickness of 1 micron, the effective Young's modulus compared to a membrane stack only containing the silicon nitride layer(s) to a thickness of 3 microns is increased by 20%.

In an embodiment, the respective layer compositions of the first layer stack 130 and the second layer stack 130' are chosen such that the membranes of the first group of CMUT cells 100 have a first spring constant (effective Young's modulus) and the membranes of the second group of CMUT cells 100' have a second spring constant (effective Young's modulus) that is no more than 20% different to the first spring constant. More preferably, the membranes of the second group of CMUT cells 100' have a second spring constant that is no more than 10% different to the first spring constant. In some embodiments, the first spring constant and the second spring constant are approximately the same, i.e. are less than 1% different to each other. This is particularly advantageous where the transducer elements of the transducer array 10 are formed by clusters of the CMUT cells 100 and 100', which transducer elements are typically addressed by a single control signal, e.g. a single bias voltage to drive the respective CMUT cells of the transducer element into collapse mode, as the comparable spring constants of the CMUT cells 100 and 100' ensure that all cells of the transducer element can remain collapsed onto the substrate 101 during operation of the transducer element, e.g. in a transmission mode or a reception mode of the ultrasound transducer array 10, i.e. exhibit comparable dynamic 'collapse' behaviour.

Any suitable 'heavy' material, i.e. a material having a relatively high density, such as a density of at least 7 g/cm$^3$, preferably a density of at least 10 g/cm$^3$, more preferably a density of at least 15 g/cm$^3$ may be used as the mass layer 135. The mass layer preferably further has a Young's modulus of less than 200 GPa Dense materials having a Young's modulus of less than 100 GPa are particularly preferred. The Young's modulus may be determined (e.g. by room temperature) using a nano-indentation measurement as per ISO14577 or ASTM E2546-07, for example. The material may be an elemental material or a composite or alloy material. The material for example may be a metal (or metal alloy) having a high density and a low Young's modulus, e.g. gold or platinum, with gold being considered particularly suitable. It is nevertheless reiterated for the avoidance of doubt that the mass layer 135 is not necessarily a metal or metal alloy; the use of any suitable material having a suitably high density and low Young's modulus may be contemplated.

As shown in FIG. 2, the second layer stack 130' may be identical to the first layer stack 130 but further include the mass layer 135. In such an embodiment, the spring constant of the second layer stack 130' will differ by a small amount from the spring constant of the first layer stack 130 due to the presence of the additional mass layer 135. For this reason, the thickness of the mass layer 135 preferably is kept as small as possible to minimize the impact on the bending stiffness, i.e. spring constant, of the second layer stack 130'.

However, it should be understood that the layer composition of the first layer stack 130 may be more substantially different to the layer composition of the second layer stack 130'; for example, the first layer stack 130 may comprise one or more layers of a dielectric material having a different thickness than the corresponding layers in the second layer stack 130' and/or the first layer stack 130 may comprise one or more layers of a dielectric material not present in the second layer stack 130' or vice versa. Although this may require a more involved manufacturing process, in this manner the respective bending stiffnesses, i.e. spring constants, of the first layer stack 130 and the second layer stack 130' including the mass layer 135 may be tuned to have a minimal difference, e.g. be (approximately) identical. As a simple example, the first layer stack 130 may comprise a layer of a dielectric material to a first thickness and the second layer stack may comprise a layer of the same dielectric material to a second thickness that is smaller than the first thickness, wherein the second thickness may be chosen such that the combination of the layer of the dielectric material to the second thickness and the mass layer 135 exhibit a bending stiffness that is (approximately) the same as the bending stiffness of the layer of the dielectric material to the first thickness in the first layer stack 130.

Figure 3:
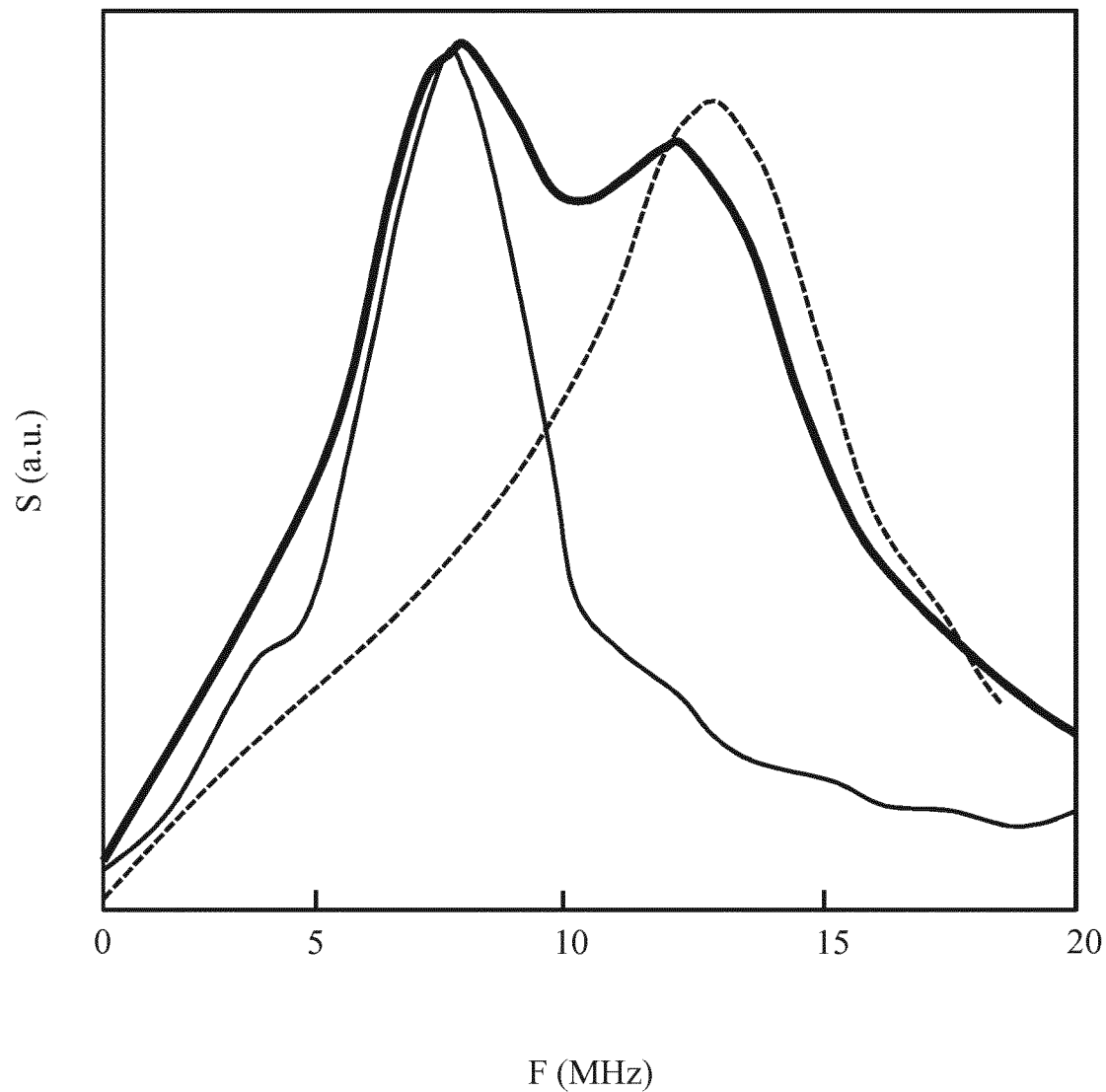
FIG. 3 is a graph depicting an operating characteristic of an ultrasound transducer array according to an embodiment.

FIG. 3 depicts the FEM-calculated frequency response of an ultrasound transducer array of CMUT cells 100 all having the same membrane without a mass layer (dashed line), the frequency response of an ultrasound transducer array of CMUT cells 100' all having this membrane onto which a mass layer 135 consisting of a 1.5 micron thick gold layer is formed (thin solid line) and the frequency response of an ultrasound transducer array comprising an alternating pattern of such CMUT cells 100 and CMUT cells 100' (thick solid line). The frequency response was obtained by driving the respective transducer arrays in collapse mode with a DC bias voltage and by applying an AC stimulus to the collapsed CMUT cells of the respective transducer arrays.

As can be seen from FIG. 3, the application of the mass layer 135 shifts the peak resonance frequency of the CMUT cells 100 from about 13 MHz to about 7 MHz for the CMUT cells 100' including the mass layer 135. The combination of the CMUT cells 100 and the CMUT cells 100' in the single ultrasound transducer array identified by the thick solid line exhibits a frequency response having a bandwidth that is nearly doubled compared to the ultrasound transducer arrays comprising CMUT cells 100 or CMUT cells 100' only. This clearly demonstrates that the presence of the first group of CMUT cells 100 as well as the second group of CMUT cells 100' within a single transducer array 10 improves the broadband characteristics of this array. It is further noted that the deployment of such multiple groups of cells within a single transducer array 10 may further be used to shape the frequency response of such an array. For example, the frequency response may be shaped to have an asymmetric profile towards a low point, e.g. −3 dB, in the frequency response. Such an asymmetric profile for example may facilitate a more harmonic wave shape at the first harmonic frequency of the array.

Figure 4:
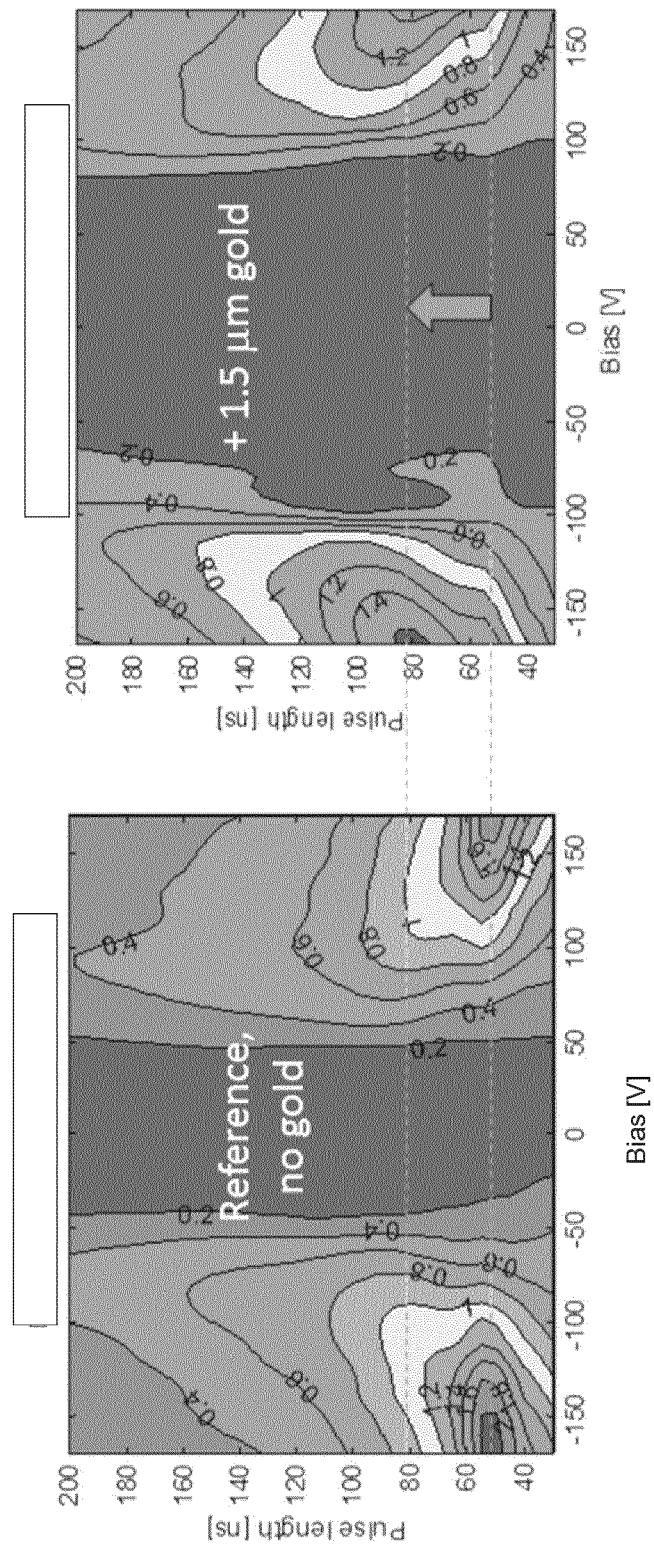
FIG. 4 is an output pressure contour plot of a CMUT array with (right pane) and without (left pane) a high density layer of its CMUT membranes.

FIG. 4 is a contour plot of the output pressure of a transducer array 10 solely comprising the first group of CMUT cells 100 (left pane) and of a transducer array 10 solely comprising the second group of CMUT cells 100' including the mass layer 135 in their respective membranes (right pane). The horizontal axis depicts the applied bias voltage [V] and the vertical axis depicts the generated pulse length [ns]. The lower dashed line horizontally extending through both contour plots denotes the central frequency of the first group of CMUT cells 100 and the upper dashed line horizontally extending through both contour plots denotes the central frequency of the second group of CMUT cells 100'. As indicated by the block arrow, the central frequency of such CMUT cells may be effectively shifted to a lower value by the inclusion of a mass layer 135 in such cells, thereby demonstrating that the broadband characteristics of an ultrasound transducer array 10 may be increased by the inclusion of multiple groups of CMUT cells within the array, wherein only some of the groups have membranes including such a mass layer 135.

Figure 5:
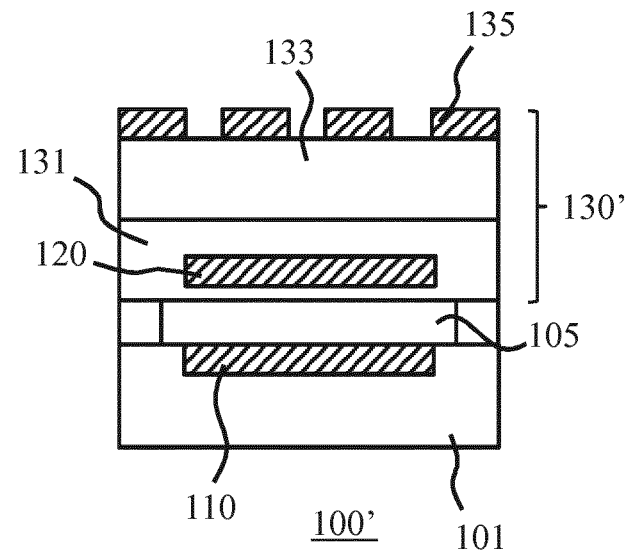
FIG. 5 schematically depicts a cross-section of part of an ultrasound transducer array according to another embodiment.

FIG. 5 schematically depicts a cross-section of another embodiment of a CMUT cell 100', in which the mass layer 135 is a patterned layer. This for example may be advantageous in case the second group of CMUT cells 100' is to be divided into a first sub group in which the respective membranes of the CMUT cells 100' have a mass layer 135 of a first mass and a second sub group in which the respective membranes of the CMUT cells 100' have a mass layer 135 of a second mass that is smaller than the first mass. Rather than having to deploy mass layers 135 of different thicknesses to achieve such different masses, the respective mass layers 135 may be formed to a single thickness, with the mass layers 135 of the CMUT cells 100' of the second sub group being patterned in order to reduce the mass of these layers. As will be immediately apparent to the skilled person, the pattern density and/or shape may be controlled in order to tune the reduction in mass of the mass layers 135 of the CMUT cells 100' of the second sub group. The patterned layer in some embodiments may be a pattern of concentric rings or a radial pattern of spokes or strips radially extending from the center of the membrane upper surface. A particular pattern may be chosen to impart a desirable stress profile onto the membrane, as will be readily understood by the skilled person.

Figure 6:
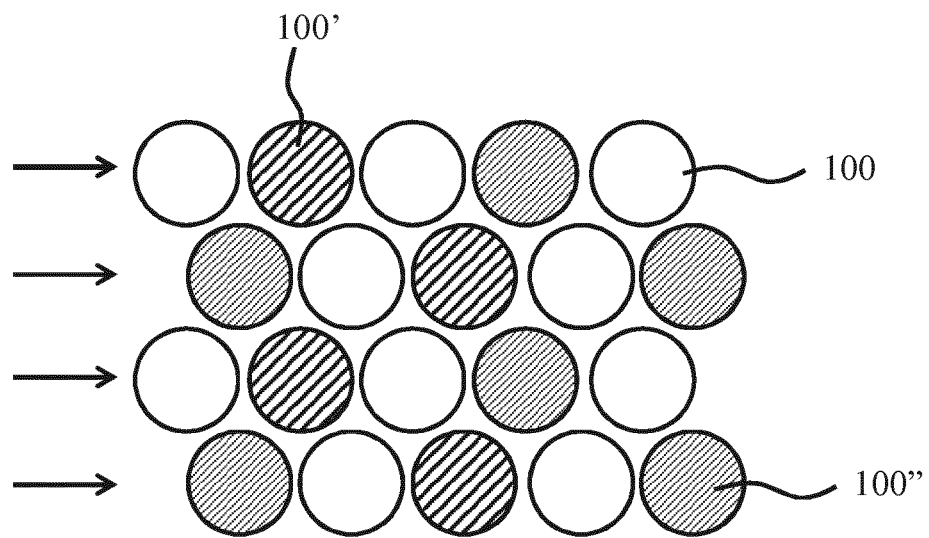
FIG. 6 schematically depicts a top view of an ultrasound transducer array according to another embodiment.

In this manner, an ultrasound transducer array 10 may be formed in which multiple groups of CMUT cells including mass layers 135 of different masses are present. FIG. 6 schematically depicts an example embodiment of such an ultrasound transducer array 10, in which the array comprises a first group of CMUT cells 100 without a mass layer in their respective membranes, a second group of CMUT cells 100' including a continuous mass layer 135 in their respective membranes and a third group of CMUT cells 100" including a patterned mass layer 135 in their respective membranes. The inclusion of multiple groups of CMUT cells having different central frequencies allows for a fine-grained tuning of the desired frequency characteristics, e.g. broadband characteristics, of the ultrasound transducer array 10. It will be immediately apparent to the skilled person that although the example ultrasound transducer array 10 in FIG. 6 comprises two different groups of CMUT cells including mass elements of different mass, embodiments in which such an ultrasound transducer array comprises more than two different groups of CMUT cells including mass elements of different mass, e.g. three groups, four groups, five groups, and so on, are equally feasible.

Figure 7:
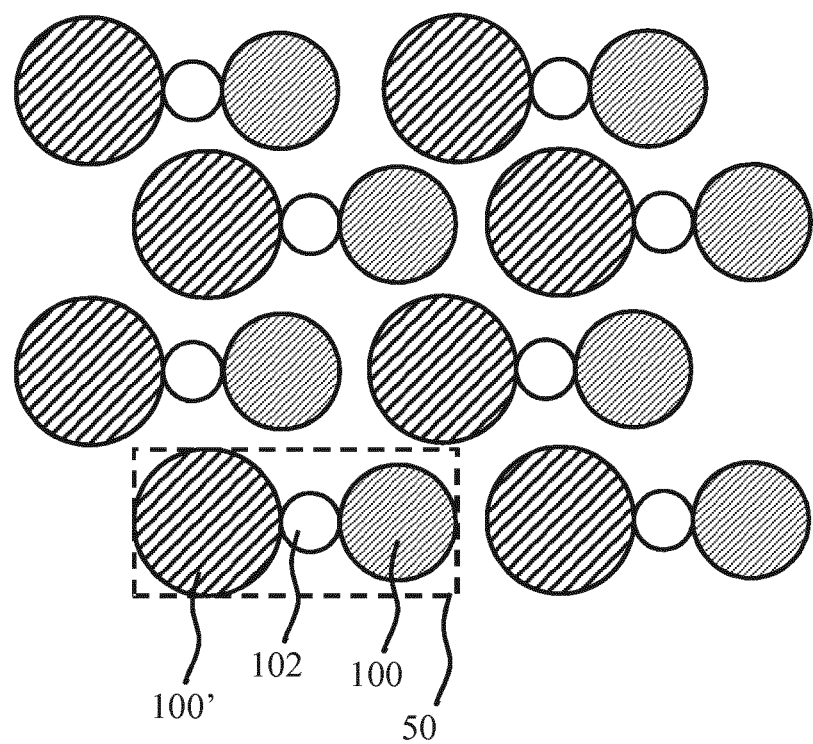
FIG. 7 schematically depicts a top view of an ultrasound transducer array according to yet another embodiment.

In an alternative embodiment, which is schematically depicted in FIG. 7, the first group of CMUT cells 100 and the second group of CMUT cells 100' have different diameters. A pair of CMUT cells 100 and 100' may form a unit cell (transducer element) 50. An interconnection 102 may be present within the unit cell 50, e.g. in between the CMUT cells 100, 100', to connect the CMUT cells to circuitry in the underlying substrate, e.g. an ASIC or the like. In this embodiment, the pitch between CMUT cells within a single group preferably is constant to ensure that the frequency characteristics of the ultrasound transducer array 10 across its transducer surface are substantially homogenous. The use of groups of CMUT cells having different diameters provides additional design freedom when adding the mass layer 135 to selected group(s) of the CMUT cells. This may be used to compensate for the fact that during collapse mode, the center frequency of CMUT cells becomes largely independent of membrane radius. This can be understood from Equation (1), where the collapse radius Rc for a small radius membrane is much smaller than for a large radius membrane, such that the term $(1-x^2)$ compensates the term $R^2$ in equation (1), thus leading to the center frequency becoming largely insensitive to the membrane radius when the CMUT cells are operated in collapse mode.

Figure 8:
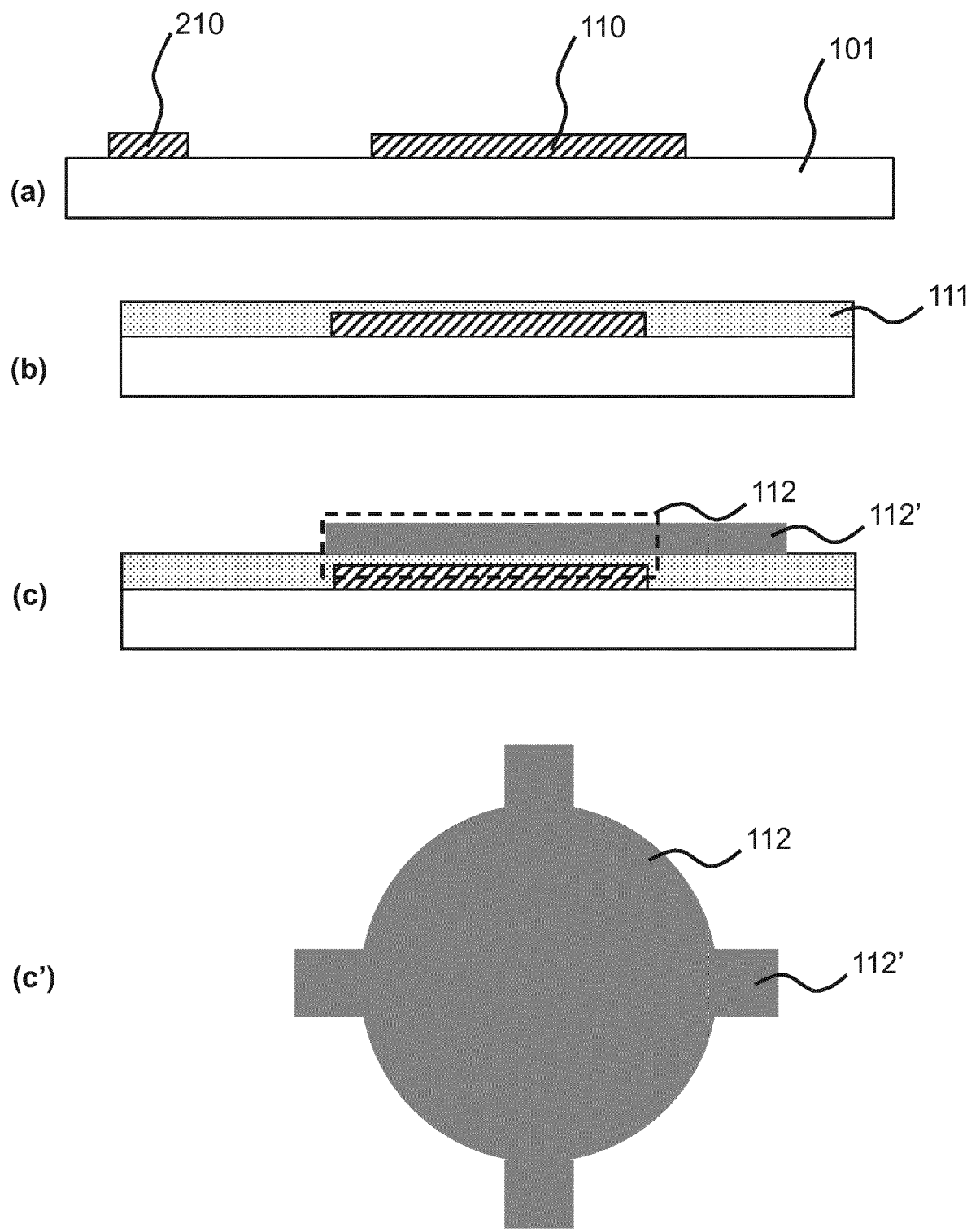
FIG. 8 schematically depicts an example manufacturing process for such an ultrasound transducer array.
Figure 8:
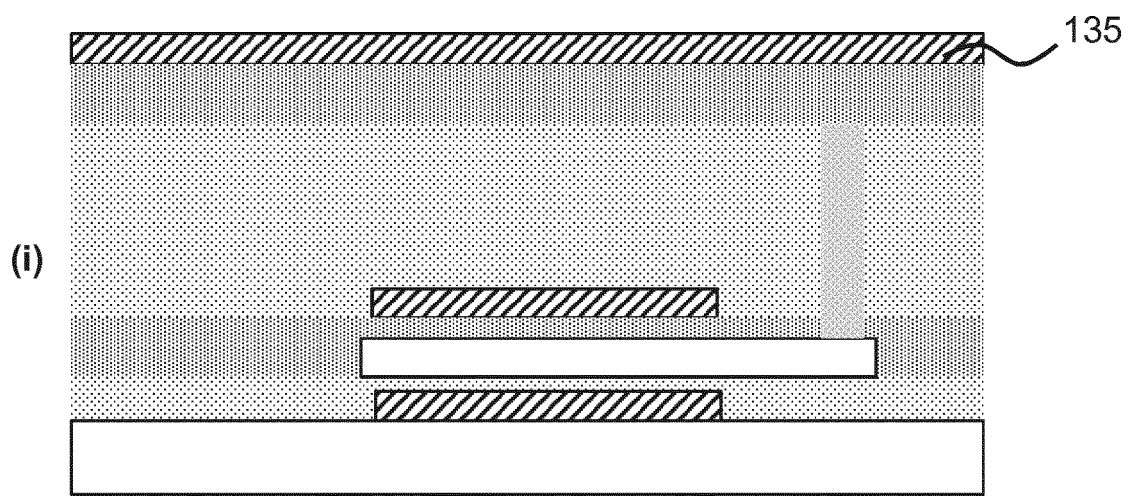

FIG. 8 schematically depicts a non-limiting example embodiment of a CMUT transducer array manufacturing method. The method proceeds in step (a) with the provision of a substrate 101, which may be any suitable substrate such as a silicon substrate, a silicon-on-insulator substrate, a silicon germanium substrate, a gallium nitride substrate and so on. A silicon-based substrate may for instance be used in a CMOS manufacturing process. The substrate 101 may comprise several structures, such as semiconductor devices, a metallization stack interconnecting the semiconductor devices and/or the CMUT cells, a passivation stack over the metallization stack and so on. The substrate 101 may for instance be the substrate of an application specific integrated circuit (ASIC) including the CMUT cells 100, 100' and 100" if present on its layer stack, e.g. passivation and/or planarization stack, wherein the CMUT cells may be connected to signal processing circuitry on the substrate 101 by the metallization stack. The provision of such substrates 101 is well-known per se and belongs to the routine skills of the skilled artisan such that the provision of suitable substrates 101 will not be discussed in further detail for the sake of brevity only.

A first electrode 110 is formed on the substrate 101, which electrode may be formed from any suitable electrically conductive material, e.g. metals or metal alloys, doped semiconductor materials such as doped poly-silicon, (semi) conducting oxides and so on. It is for instance particularly advantageous to use metals that are readily available in the manufacturing technology of choice, as this requires minimal redesign of the manufacturing flow, which is attractive from a cost perspective. For example, in a CMOS process, conductive materials such as Al, W, Cu, Ti, TiN and so on, as well as combinations of such materials, may be used to form the first electrode 110.

The formation of the first electrode 110 may form part of the formation of a first electrode arrangement over the substrate 101, which first electrode arrangement includes the respective first electrodes 110 of the CMUT cells 100, 100', 100".

The first electrode 110, and the substrate 300 may subsequently optionally be covered by an electrically insulating (dielectric) material layer 111. This is shown in step (b). Such a dielectric layer 111 for instance may be used to electrically insulate the first electrode 110 from its counter electrode 120 (see below) to reduce the risk of short circuits between the electrodes during the operation of the CMUT cell. In addition, the dielectric layer 111 may be used to protect the first electrode 110 and the substrate 101 from damage during the removal of the sacrificial material to form the cavity over the first electrode 110.

Although the dielectric layer 111 is shown to cover the entire substrate surface 101, it is equally feasible to provide a patterned dielectric layer 111 in which only certain parts of the substrate 101 together with the first electrode 110 are covered by the dielectric layer 111. Any suitable dielectric material may be used for the protection of the first electrode 110 and the substrate 101, e.g. one or more materials selected from silicon nitride ($Si_3N_4$), silicon oxide (Sift), aluminium oxide ($Al_2O_3$), hafnium oxide ($HfO_2$) or the like, although it is emphasized that the suitable dielectric materials are not limited to these example materials. In addition, mixtures or laminates of the aforementioned dielectric materials may be used for the protection of the first electrode 110. As such a dielectric layer 111 may be formed in any suitable manner, e.g. using suitable deposition techniques such as ALD, (PE)ALD, PLD, PVD, LPCVD and PECVD, its formation will not be explained in further detail for the sake of brevity.

In step (c), a sacrificial material is formed, e.g. through a suitable deposition technique, on the substrate 101 including the first electrode 110 and the optional dielectric layer 111. The sacrificial material is patterned to include a first region 112 over the first electrode 110 from which the cavity is formed and may further comprise a second region 112' outside the intended cavity area acting as a channel through which the sacrificial material may be removed. The height of the sacrificial material layer corresponding to the gap height of the cavity to be formed is typically in the range of 100-1,000 nm although it should be understood that values outside this range may also be contemplated.

In an embodiment, the first region 112 is a circular region with the second region 112' extending from the first region 112 in the form of one or more teeth-like protrusions, e.g. 2-8 of such protrusions. A top-view of such a sacrificial material portion is shown in step (c'), in which four of such protrusions are shown by way of non-limiting example only. The teeth-like second regions 112' are typically used as cavity access platforms outside the membrane to be formed through which access to the first portion 112 can be provided for opening or releasing the cavity.

In principle, any suitable sacrificial material may be used, although for device performance reasons it is preferable to use sacrificial materials that can be effectively removed in a subsequent etching step. For instance, the use of metals such as Al, Cr and Mo, Ti and (Ti)W or non-metals such as amorphous silicon or silicon oxide may be contemplated. Materials such as Al, amorphous silicon and silicon oxide are for instance readily available in CMOS processes, and of these materials Al can be particularly effectively removed by etching. The patterned sacrificial material may be formed in any suitable manner, e.g. using suitable deposition and patterning techniques and its formation will not be explained in further detail for the sake of brevity.

It will be understood that the diameter of the first region 112 defines the diameter of the cavity of a CMUT cell 100, 100', 100" to be formed. In an embodiment, the diameter is selected in a range of 20-500 micron, more preferably in a range of 50-300 micron, although it should be understood that larger diameters may also be contemplated, e.g. diameters up to 1,000 micron.

In step (d), a first dielectric layer 131 of the membrane to be formed is deposited over the first region 112 and the second region 112' of the sacrificial material and the exposed portions of the dielectric layer 111 if present. As the first dielectric layer 131 and the dielectric layer 111 are both exposed to the etch recipe for removing the sacrificial layer, the first dielectric layer 131 and the dielectric layer 111 may be of the same material, although it is of course also plausible to use different materials for the first dielectric layer 131 and the dielectric layer 111 respectively. In an embodiment, the first dielectric layer 131 and the dielectric layer 111 each comprise at least one layer formed any suitable dielectric material, such as a silicon oxide layer, e.g., Sift, a silicon nitride layer, e.g., $Si_3N_4$ or the like, an aluminium oxide ($Al_2O_3$) layer, a hafnium oxide ($HfO_2$) layer and so on. Many other suitable dielectric layer materials will be apparent to the skilled person. Preferably, deposition techniques such as PECVD and ALD are used to form the dielectric layers as these techniques can be performed at temperatures below 400° C., which makes them compatible with CMOS manufacturing processes. The first dielectric layer 131 may be formed as a layer stack, e.g. an oxide-nitride stack or an oxide-nitride-oxide stack. Similarly, the optional dielectric layer 111 may be formed as such a stack. It is reiterated that any suitable dielectric material may be used for the optional dielectric layer 111 and the first dielectric layer 131. In addition, mixtures or laminates, e.g.

ALD laminates, of the aforementioned dielectric materials may be used for these dielectric layers.

After the formation of the first dielectric layer 131, the second electrode arrangement including the second electrodes 120 is formed on the first dielectric layer 131 as shown in step (e) such that each second electrode 120 is oriented opposite a first electrode 110. The second electrode arrangement preferably is formed of the same electrically conductive material as the first electrode arrangement, although it should be understood that the second electrode arrangement and the first electrode arrangement alternatively may be formed of different materials. The second electrode arrangement may for instance be formed from any suitable electrically conductive material such as Al, W, Cu, Ti, TiN and so on, as well as combinations of such materials. The second electrode arrangement may be formed using well-known techniques that are not further explained for the sake of brevity only. The first electrode arrangement including the first electrodes 110 and the second electrode arrangement including the second electrodes 120 may be formed to any suitable thickness, e.g. 50-250 nm thickness. Other suitable thicknesses may be contemplated, e.g. depending on the application domain.

After the formation of the second electrode 120, the method proceeds as shown in step (f), in which the second dielectric layer 133 is formed. In an optional embodiment, the second dielectric layer 133 is formed to a first thickness t1, which exceeds the thickness of the first portion 112 of the sacrificial material in between the first electrode 110 and the second electrode 120 such that upon formation of the cavity 130 the height g of the cavity gap is substantially smaller than the thickness t1, i.e. $g/t1 \ll 1$. Preferably $t1 \geq 3$ g, more preferably $t1 \geq 5$ g. This ensures that during the release of the cavity 105 in step (g), i.e. by formation of the access or via 116 and the subsequent removal of the first portion 112 and the second portion 112' of the sacrificial material, the membrane exhibits excellent membrane robustness during the cavity release step as $g \ll t1$ at the stage of removal of the sacrificial material to form the cavity 105. Moreover, because the second dielectric layer 133 is formed, e.g. deposited, prior to the release of the cavity 105, a membrane with excellent flatness characteristics is obtained as the presence of the sacrificial material prevents deformation of the first dielectric layer 131 during the formation of the second dielectric layer 133.

The first portion 112 and the second portions 112' of the sacrificial material are subsequently removed as shown in step (g) by the formation of the access or via 116 using a suitable etch recipe to form the cavity 105 in between the first electrode 110 and the second electrode 120 embedded in between the first dielectric layer 313 and the second dielectric layer 315 of the membrane layer stack 130 of the CMUT cells 100, 100'. Suitable etch recipes for such conventional sacrificial materials are well-known per se and the skilled person will have no difficulty selecting an appropriate etch recipe using his common general knowledge.

The thickness of the layer stacks 130 may be further increased during the sealing of the access or via 116 in step (h) by the formation of the further dielectric layer 134 including the plug 118 in the access or via 116. The further dielectric layer 134 may be substantially thinner than the second dielectric layer 133. The further dielectric layer 134 may be formed to a thickness of at least twice the height, e.g. 3-4 times the height, of the cavity 105 to effectively seal the access or via 116.

In step (i), a mass layer 135 is applied to selected membrane layer stacks 130 in order to form the membrane layer stacks 130' of the second group of CMUT elements 100. Such a mass layer 135 may be selectively applied in any suitable manner, e.g. by applying a mask layer across the membrane layer stacks 130, and patterning this mask layer to expose the membrane layer stacks 130 to which the mass layer 135 is applied, after which application the mask layer may be removed. Other suitable techniques for selectively applying the mass layer 135 will be immediately apparent to the skilled person. Although not explicitly shown, a further differentiation in the second group of CMUT cells 100' may be achieved by patterning selected mass layers 135 to form a first sub group and a second sub group of CMUT cells comprising mass layers 135 with different masses as previously explained.

At this point it is emphasized that steps (a)-(i) schematically depict an advantageous but non-limiting example of forming one or more CMUT cells 100, 100' and 100" if present on a substrate 101. Many alternative routes will be apparent to the skilled person.

A notable process variation is that the access or via 116 may be sealed in any suitable manner using any suitable material, e.g. by depositing and patterning a dedicated sealing layer such as a metal or dielectric layer to form the plug 118. It is furthermore noted that the cavity 105 may be released at any suitable point in the CMUT manufacturing process, e.g. prior to the formation of the second dielectric layer 133. Another notable process variation is that the first electrode 110 and/or the second electrode 120 may or may not be separated from the cavity 130 by a dielectric layer, as this is a typical design choice. As previously mentioned, a dielectric layer, i.e. an electrically insulating layer, may be provided over the first electrode 110 and/or the second electrode 120 to prevent direct contact between the first electrode 110 and the second electrode 120 during operation of the CMUT cells 100, 100' and 100" if present.

The membrane stacks 130 may be formed in any suitable manner, e.g. by a single dielectric layer rather than a stack of dielectric layers, and so on. Such process choices fall within the routine skills of the skilled person and will therefore not explicitly mentioned in detail for the sake of brevity only. As previously mentioned, not all CMUT cells 100, 100' may have the same membrane stack 130. It is equally feasible to, in addition to the presence of the mass layer 135 in the second group of CMUT cells 100', to have different layers and/or different layer thicknesses between the layer stack 130 and 130' respectively.

Also, it should be understood that alternative designs of the individual CMUT cells 100 are of course equally feasible. The design of the CMUT cells 100 is not particularly relevant to the present invention, and any suitable design of the cells may be contemplated; for example, 3-electrode CMUT cells 100 in which an intermediate electrode is located between the bottom electrode 110 and the cavity 105 are equally feasible. Such 3-electrode CMUT cells for instance may be contemplated to provide a stimulus and a bias voltage through separate electrodes, e.g. to reduce the risk of membrane sticking to the bottom of the CMUT cell.

At this point it is further noted that although not shown in the various embodiments, it should be understood that the CMUT cells 100, 100' and 100" if present manufactured in accordance with embodiments may comprise additional circuit elements, which may be integrated on the substrate 101 or may be provided on a separate substrate and integrated into a single package with one or more of the CMUT devices from a wafer manufactured in accordance with embodiments of the present invention. Such additional circuitry may be instance be an IC, e.g. an ASIC, for controlling the one or more CMUT cells 100, 100' and 100" if present and/or processing the signals generated by the one or more CMUT cells 100, 100' and 100" if present, e.g. to control transmission and/or reception modes of the one or more CMUT cells 100, 100' and 100" if present. Other suitable embodiments of the CMUT cells 100, 100' and 100" if present and/or an ultrasound transducer array 10 comprising such cells will be immediately apparent to the skilled person.

It is furthermore noted that in the aforementioned manufacturing process, a wafer processed during the manufacturing process may contain a single die, i.e. a single device, in which case the substrate 101 corresponds to the wafer, or a plurality of dies that may be singulated in any suitable manner, e.g. diced, after the completion of the device manufacturing process, in which case the substrate 101 corresponds to a part of the wafer, an example embodiment of which will be described in more detail below.

FIG. 9 is a plan view of a two dimensional transducer array 10 of the previously described groups of circular CMUT elements 50 (which each may contain CMUT cells 100, 100' and 100" if present as previously explained) according to an embodiment. The array is configured in the conventional manner of symmetrically aligned rows 56 and columns 58 of CMUT elements. In this example each column 58 is covered with an integral flexible foil containing embedded metal tracks, which allow the columns to be bent in a cylindrical shape. The flexible foil will be described in greater detail below. In this example the array is dimensioned to have the same pitch in both the row and column directions, as indicated by arrow 52 which denotes the pitch in the column direction and arrow 54 which denotes the pitch in the row direction. The columns 58 may be formed as separate substrate islands, e.g. separate silicon islands or strips, such that the transducer array 10 may be wrapped around a three dimensional body, e.g. a cylindrical body such as an external sheath of a catheter.

FIG. 10 is a plan view of a two-dimensional ultrasound transducer array 10 that is configured in accordance with a preferred embodiment. As shown in FIG. 10, the rows 56 and columns 58 of the groups of CMUT elements 50 are staggered in alignment, as is well-known per se. The staggered alignment in this example is accommodated by increasing the spacing 55 between CMUT elements 50 in the columnar direction, which enables adjacent columns and rows to be further interspersed with each other. In an embodiment, the spacing 55 is at least the diameter D of a CMUT element 50. In the transducer array 10 comprising transducer elements 50 having multiple groups of CMUT cells 100, 100', (100" and so on), the pitch between CMUT cells 100, 100' of the same group preferably is constant in the array such that the array exhibits uniform broadband characteristics over the total transducer area of the array.

In the illustrated example the transducer elements 50 are so tightly interspersed that a tangential line from cell to cell in the column or row direction would actually intersect a cell of the adjacent staggered row or column. The interspersion of transducer elements 50 allows for an increase in the density of CMUT elements within the transducer array 10 without requiring an increase in the vertical spacing (i.e. in the column direction) between transducer elements 50, at least up to the point where the closest packing of transducer elements 50 is achieved. Beyond this point, the pitch between successive CMUT elements 50 in the columnar direction may be increased as arrow 55 shows to facilitate a further decrease in horizontal spacing, as indicated by arrows 57 and 59, but this will reduce the overall CMUT density of the transducer array. At least at its closest packing, the CMUT transducer array 10 of FIG. 10 has a greater cell density than the CMUT transducer array 10 of FIG. 9.

In FIG. 10, each column 58 of CMUT elements 50 is located on a separate substrate island, i.e. a separate piece of silicon die. The respective substrate islands, e.g. silicon islands, are characterized by having a meandering edge structure in the length direction of, i.e. along, the columns 58, with edge portions 58A meandering outwardly around transducer elements 50 and edge portions 58B meandering inwardly into a space between neighboring CMUT cells 50, 50' in a column 58. In other words, the columns 58 have wave-shaped opposing edges in the column direction where the wave peaks coincide with the CMUT cells 50, 50' and the wave valleys coincide with the spacings 55 in between the CMUT elements 50.

A neighboring column 58 is arranged such that an outwardly meandering edge portion of its silicon island aligns with, i.e. slots into, an inwardly meandering edge portion of a neighboring silicon island, thereby forming the staggered rows of CMUT elements 50 by the staggered alignment of the CMUT elements 50 between neighboring columns 58. Neighboring silicon islands are typically separated by a gap 57, to facilitate out-of-plane bending of the silicon islands respective to each other, e.g. when wrapping the CMUT transducer array 10 around a three dimensional body such as a cylindrical body, e.g. a catheter sheath.

In order to retain the relative positions of the substrate islands respective to each other, the CMUT transducer array 10 further comprises a flexible foil 60 onto which the substrate islands are mounted. The flexible foil 60 for instance may comprise a so-called flex-to-rigid foil in which a metal layer or metal layer stack, e.g. metal tracks, is embedded in or covered by a polymer layer or polymer layer stack, which polymer typically is electrically insulating in order to protect the metal layer from accidental short circuits. A non-limiting example of a suitable polymer for such a flexible foil 60 is polyimide, as it is well-known per se that polyimide is compatible with many semiconductor manufacturing processes such as a CMOS manufacturing process. Other suitable polymers, e.g. parylene, will be immediately apparent to the skilled person. A non-limiting example of a suitable metal is aluminium or any other metal commonly used in semiconductor manufacturing processes. The compatibility of such materials with existing semiconductor manufacturing processes facilitates the manufacture of the CMUT transducer array using existing semiconductor manufacturing processes rather than having to redesign or redevelop such manufacturing processes, which would increase the cost of the CMUT transducer array 10.

The provision of the CMUT elements 50 on a plurality of adjacent meandering substrate islands interconnected via a flexible foil 60 allows for the out-of-plane bending of the CMUT transducer array 10 in the row direction of the array whilst providing structural integrity in the column direction of the array, which for example is particularly advantageous when wrapping the array around a catheter such as an intra-vascular catheter or an intra-cardiac catheter. For example, the CMUT transducer array 10 may be wrapped around the external sheath of such a catheter, with the silicon island columns 58 aligning in a length direction of the catheter, i.e. CMUT transducer array 10 being bent out-of-plane and is wrapped around the catheter sheath in its row direction. Due to the provision of a large number of relatively narrow silicon islands, a near-cylindrical configuration of the CMUT transducer array 10 may be achieved when wrapping the CMUT transducer array 10 around a cylindrical body such as a catheter sheath, with the further advantage that such a CMUT transducer array is continuous over the entire surface of such a body, e.g. does not contain discontinuities between adjacent rectangular silicon islands forming part of the CMUT transducer array, as for instance is the case in EP 2 455 133 A1.

In accordance with a further aspect of the present invention, advantage is taken of this decreased spacing 57 and 59 by operating the array of FIG. 10 so that an operational row of transducer elements 50 is not a horizontal row 56 of elements but an interspersed combination of two (or more) adjacent staggered rows. This is contrary to the conventional wisdom of diced piezoceramic transducer elements, in which an operational row of elements is a perfectly linear row of elements. In the example of FIG. 10, an operational row of elements is formed by staggered rows of elements. For instance, one operational row in FIG. 4 comprises transducer elements $62_1$, $62_2$, $62_3$, $62_4$, ... $62_N$ of two adjacent staggered rows, i.e. the $M^{th}$ operational row comprises the $M^{th}$ CMUT element 50 of each column 58 of CMUT elements 50, with M being a positive integer, with each row typically forming a meandering annular row when wrapped around a catheter. The tighter spacing of the staggered rows enables an operational row of 96 cells to be provided where the standard symmetrical alignment would only accommodate 64 cells, for instance, and the staggered configuration of the operational row still is capable of providing acoustic signals for highly resolved images with lower clutter due to the reduced grating lobes in the antenna pattern. Such a staggered row for instance may be addressed by sequentially activating the appropriate CMUT elements 50 of neighboring columns 58, e.g. sequentially activate transducer elements $62_1$, $62_2$, $62_3$, $62_4$, ... $62_N$ of the N columns 58.

In the embodiment of FIG. 10, the respective substrate, e.g. silicon, islands are retained by a continuous flexible foil 60. In an alternative embodiment, the flexible foil 60 may be patterned such that the flexible foil 60 comprises a plurality of recesses aligning with the gaps 57, with respective bridge portions or bridges extending across the gaps 57 to interconnect different regions of the flexible foil 60, e.g. different regions retaining different substrate (silicon) islands. This further increases the flexibility of the CMUT transducer array 10 but may be less robust.

FIG. 11 illustrates several process steps in the formation of a flexible foil bridge joining two silicon islands on which CMUT elements 50 are located. FIG. 11(a) shows a silicon wafer 70 with thermal silicon dioxide layers 72 grown on the top and bottom sides. Patterned aluminum areas 81 are sputtered on the top side using standard lithography. A patterned area of polyimide 74 is laid over one of the aluminum areas on the top side, which pattern defines the bridges in the flexible foil. In case of a continuous flexible foil, the polyimide 74 may be a continuous sheet. An aluminum layer 80 is deposited over the polyimide 74 and a second polyimide layer 76 is laid over the aluminum. Another layer of aluminum 82 is patterned over the aluminum layer 80 for use as a mask during etching, all as shown in FIG. 11(b).

Finally, as shown in FIG. 11(c), the silicon wafer 70 is etched away from the back in areas outside the masked by thick resist areas 84, both under CMUT location 88 and under the flexible bridge 74, 80, 76. The polyimide layer 76 on either side of the flexible bridge 90 on the top side is patterned away on either side of etch mask layer 82, which is then itself etched away. The result is two separate silicon islands 92 and 94, joined by a flexible bridge 90. The flexible bridge 90 and others like it enable an array of such CMUT-populated islands to be wrapped in a cylindrical shape, fitting the needs of an intra-cardiac catheter transducer.

Figure 12:
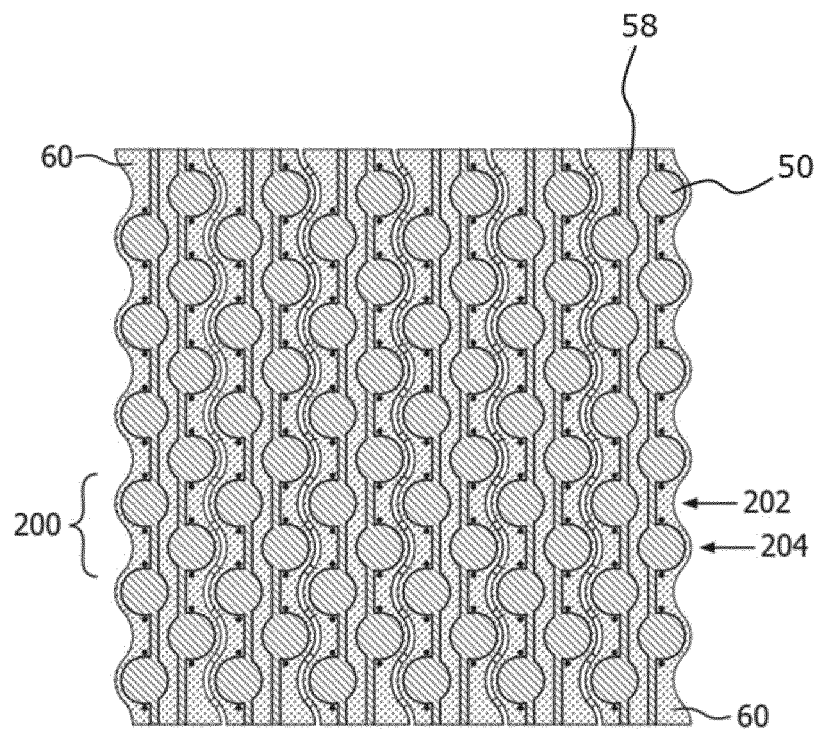
FIG. 12 illustrates the operation of adjacent staggered rows of CMUTs as a single row of transducer elements in accordance with an embodiment.

As previously mentioned, an operational row 200 of acoustic transducer elements 50 is formed, not by a straight line of transducer elements as in the conventional manner, but by two or more adjacent staggered rows 202 and 204 of CMUT cells 50, 50'. FIG. 12 schematically depicts an alternative embodiment of an ultrasound transducer array 10 in which each silicon island column 58 comprises a pair of CMUT element 50 comprising columns arranged in a staggered arrangement, i.e. the area of a CMUT element 50 in a first column extends into the space between neighboring CMUT element 50 in the neighboring column, preferably such that a tangent between these neighboring CMUT cells intersects the area of the CMUT element 50 extending into the space between these neighboring CMUT elements.

As before, the silicon island columns 58 have a meandering edge structure in the length direction of, i.e. along, the columns 58, with edge portions meandering outwardly around CMUT elements 50 and edge portions meandering inwardly into a space between neighboring CMUT elements 50 in a column 58. A neighboring column 58 is arranged such that an outwardly meandering edge portion of its silicon island aligns with, i.e. slots into, an inwardly meandering edge portion of a neighboring silicon island, thereby forming the staggered rows of CMUT elements 50 by the staggered alignment of the CMUT elements 50 between neighboring columns 58. Neighboring silicon islands are typically separated by a gap 57, to facilitate out-of-plane bending of the silicon islands respective to each other, e.g. when wrapping the CMUT transducer array 10 around a catheter sheath as previously explained.

This embodiment has the advantage of providing larger, i.e. wider, silicon islands, which improves the structural rigidity of such islands, whilst still providing an ultrasound transducer array with excellent flexibility in the row direction. This embodiment is particularly advantageous where the circumference of a body, e.g. a catheter sheath, around which the transducer array is to be wrapped, is many times the width of a single silicon island, such that many silicon islands are to be wrapped around the body, and such that substantially continuous transducer rows are provided around the body.

Figure 13:
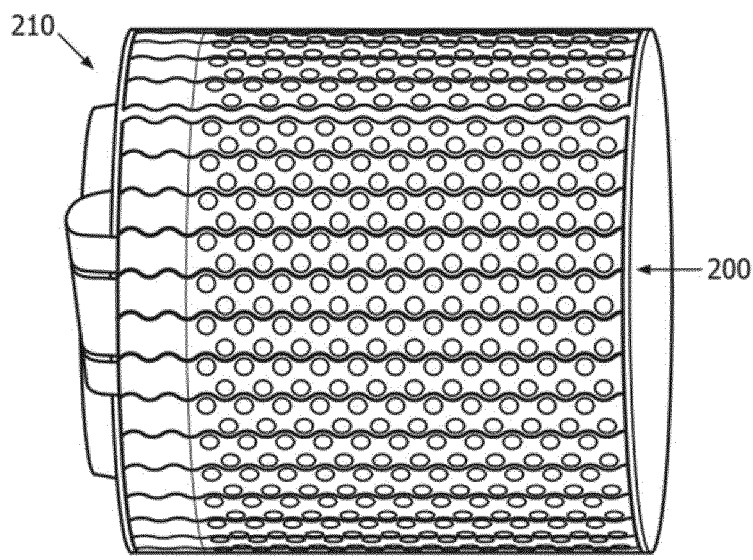
FIG. 13 illustrates the CMUT array of FIG. 12 when wrapped in a cylindrical configuration.

As before, the direction of operational row 200 is the in-plane, beam-steering direction, i.e. beam steering typically takes place perpendicular to the columns 58. The separate silicon islands are overlaid with a flexible foil 60, e.g. a continuous foil as shown in the drawing or a patterned foil containing bridge portions 90 across the gaps between neighboring silicon islands, to retain the respective orientation of the silicon islands and to enable the two dimensional transducer array 10 to be bent into a cylindrical shape around a distal tip 210 of a catheter 250 as shown in FIG. 13. It should be understood that the array is wrapped around the distal tip 210 by way of non-limiting example only; it is for instance equally feasible to wrap the transducer array 10 around any other part of the catheter 250, even though it is preferred that the array 10 is located proximal to the distal tip of the catheter 250. In some embodiments, the catheter 250 may comprise a further ultrasound transducer array (not shown) on the distal tip 210, e.g. a planar ultrasound transducer array having a circular circumference in addition to the wraparound ultrasound transducer array 10, such that the catheter 250 can generate images of a body portion ahead of the catheter as well as around the catheter, which for instance is particularly advantageous in intra-cardiac imaging. In some embodiments, the catheter 250 therefore may be an intra-cardiac or intravascular catheter.

Figure 15:
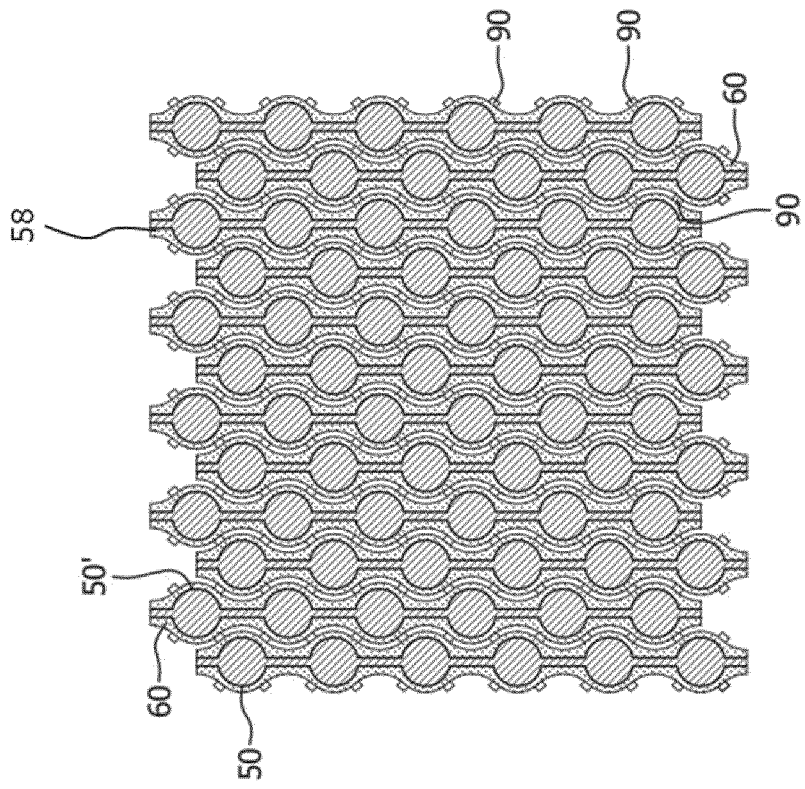
FIG. 15 is a plan view of a CMUT array according to an embodiment of the present invention with multiple cells located on each silicon island and with a flexible foil overlay joined by flexible metallic bridges.
Figure 14:
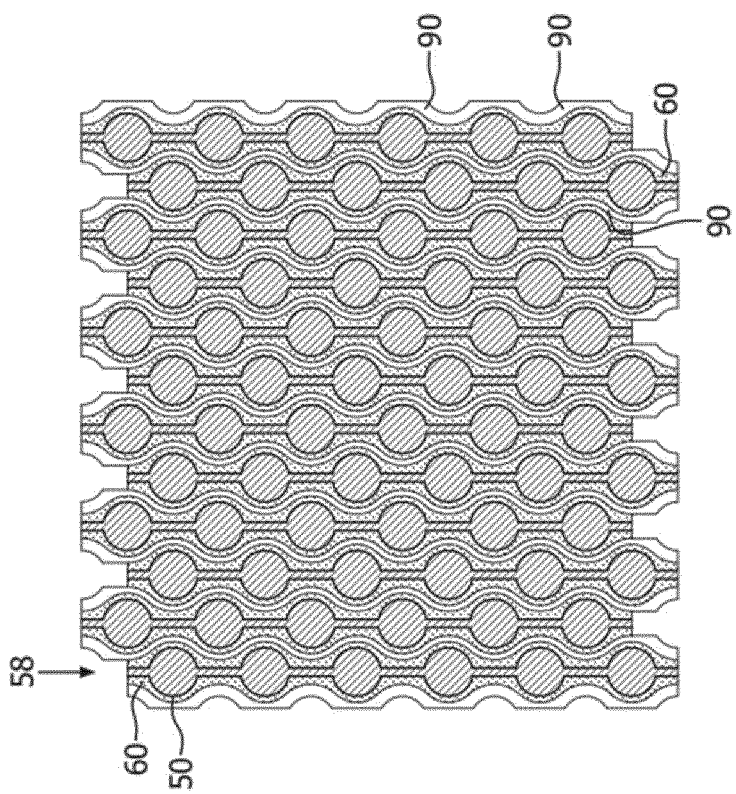
FIG. 14 is a plan view of a CMUT array according to an embodiment of the present invention with each cell located on its own silicon island and with a flexible foil overlay joined by flexible metallic bridges.

FIGS. 14 and 15 are plan views of two CMUT arrays 10 according to further embodiments of the present invention. In FIG. 14 each CMUT element 50 is fabricated on its own substrate, e.g. silicon, island 92 (see FIG. 11). Each column 58 of CMUT elements 50 is overlaid with a strip 60 of flexible foil and the foil strips of adjacent columns are interconnected by flexible bridges 90 which are formed as shown in FIG. 11. The flexible foil strip 60 can comprise a conductive material, such as aluminum, which allows either to address ultrasound elements together within the column, or keeping the elements at the same potential, such as ground. The individual addressing of the elements 50 in the transducer array 10 may be realized via the integrated circuitry. The flexible bridges thus help maintain the orientations of the elements 50 of the transducer array 10 while permitting the array to be flexed and bent in a curved configuration. In particular, in this embodiment the CMUT transducer array 10 may be bent in the row direction as well as in the column direction due to each column 58 being formed by multiple substrate islands interconnected by the bridge structures 90 in the flexible foil strip 60.

FIG. 15 shows a similar CMUT array 10, except that there are two CMUT elements 50, 50' on each substrate, e.g. silicon, island 92. For instance, CMUT elements 50 and 50' of adjacent columns of elements are both located on the same silicon island. The two adjacent columns are overlaid with a flexible foil strip 60, and adjacent foil strips are interconnected by flexible bridges 90 which permit bending of the CMUT transducer array 10 into a curved or cylindrical shape.

As before, it should be understood that instead of a flexible foil strip 60 having discrete portions interconnected by bridge structures 90, a continuous flex foil may be used to retain the respective substrate islands. Such an alternative embodiment is more robust but may have more limited flexibility. This however may not be problematic if the curvature of the body onto which the CMUT transducer array 10 is to be fitted is relatively limited.

At this point, it is further noted that although the embodiments in FIG. 9-15 have been described in terms of CMUT elements 50 comprising clusters of CMUT cells 100, 100', it is equally feasible that each CMUT element 50 comprises a single CMUT cell, e.g. a CMUT cell 100 or a CMUT cell 100', in which the transducer array 10 typically comprises an alternating pattern of CMUT cells 100, 100' as the CMUT elements 50.

Figure 16:
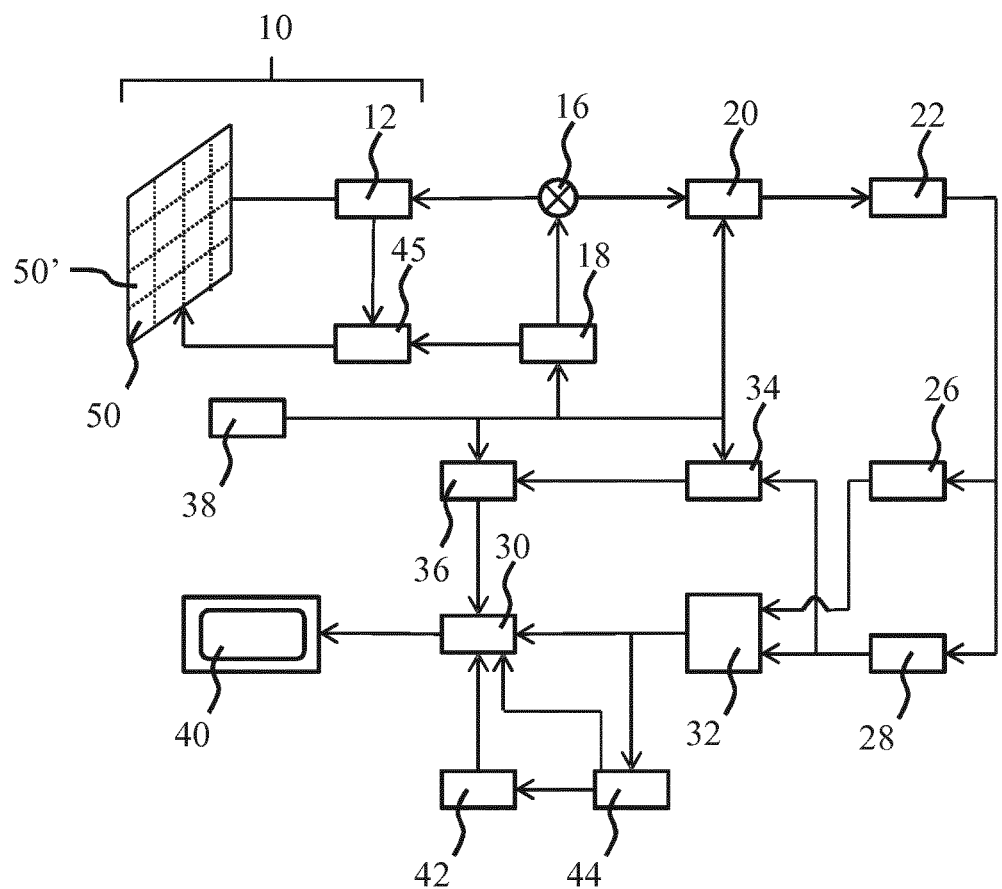
FIG. 16 is a block diagram of an ultrasound imaging system according to an embodiment.

FIG. 16 schematically depicts an example embodiment of an ultrasonic diagnostic imaging system 1 with an ultrasound transducer array 10, e.g. an array of ultrasound transducer element tiles (transducer elements) comprising multiple CMUT cells 100 and/or 100' connected together and operated in unison as a single transducer element, in block diagram form. The array 10 may form part of an ultrasound probe such as a catheter 250 as previously explained. In FIG. 16, the transducer array 10 is provided for transmitting ultrasonic waves and receiving echo information. As previously explained, the transducer array 10 may be a one- or a two-dimensional array of ultrasound transducer element tiles capable of scanning in a 2D plane or in three dimensions for 3D imaging.

The transducer array 10 may be coupled to a microbeam former 12, which may be integrated in a probe or catheter 250, which controls transmission and reception of signals by the ultrasound transducer cells 100 (or clusters thereof). Microbeam formers are capable of at least partial beam forming of the signals received by groups or "patches" of transducer element tiles for instance as described in U.S. Pat. No. 5,997,479 (Savord et al.), U.S. Pat. No. 6,013,032 (Savord), and U.S. Pat. No. 6,623,432 (Powers et al.)

The microbeam former 12 may be coupled by a probe cable, e.g. coaxial wire, to a terminal, e.g. a patient interface module or the like, comprising a transmit/receive (T/R) switch 16 which switches between transmission and reception modes and protects the main beam former 20 from high energy transmit signals when a microbeam former is not present or used and the transducer array 10 is operated directly by the main system beam former 20. The transmission of ultrasonic beams from the transducer array 10 under control of the microbeam former 12 may be directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array 10, or at different angles for a wider field of view. The transducer controller 18 may be coupled to control the voltage source 45 for the ultrasound transducer array 10. For instance, the power supply 45 sets the DC and AC bias voltage(s) that are applied to CMUT elements of a CMUT array 10, e.g. to operate the one or more CMUT cells 100, 100' of the CMUT elements in collapse mode, as is well-known per se.

To this end, the power supply 45 may optionally comprise separate stages for providing the DC and AC or stimulus components respectively of the drive voltage of the CMUT cells 100, e.g. in transmission mode. A first stage may be adapted to generate the static (DC) voltage component and a second stage may be adapted to generate an alternating variable voltage component or stimulus having a set alternating frequency, which signal typically is the difference between the overall drive voltage and the aforementioned static component thereof. The static or bias component of the applied drive voltage preferably meets or exceeds the threshold voltage when forcing the CMUT elements into their collapsed states, i.e. when operating the CMUT elements in collapsed mode. This has the advantage that the first stage may include relatively large capacitors, e.g. smoothing capacitors, in order to generate a particularly low-noise static component of the overall voltage, which static component typically dominates the overall voltage such that the noise characteristics of the overall voltage signal will be dominated by the noise characteristics of this static component.

Other suitable embodiments of the power supply 45 should be apparent, such as for instance an embodiment in which the power supply 45 contains three discrete stages including a first stage for generating the static DC component of the CMUT drive voltage, a second stage for generating the variable DC component of the drive voltage and a third stage for generating the frequency modulation or stimulus component of the signal, e.g. a pulse circuit or the like. It is summarized that the power supply 45 may be implemented in any suitable manner.

The partially beam-formed signals produced by the microbeam former 12 may be forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of ultrasound transducer cells 100, 100'. In this way the signals received by thousands of transducer elements of a transducer array 10 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be forwarded to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the transducer array 10 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system 1 is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound transducer array 10 may not have 3D imaging capabilities and so on. Other variations will be apparent to the skilled person.

The ultrasound transducer array 10 according to embodiments of the present invention may form part of a catheter as previously explained. As will be readily understood by the skilled person, such a transducer array may form part of any type of investigative device, e.g. an ultrasound probe, an ultrasound matrix probe, an ultrasound catheter, an ultrasound needle, and so on. Such an ultrasound transducer array 10 may be used in any suitable ultrasound imaging technique.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A transducer array, comprising a plurality of CMUT cells suitable for a collapsed operation mode, each CMUT cell comprising a first electrode supported by a substrate and a second electrode supported by a membrane suspended over a cavity between the first electrode and the second electrode, the plurality of CMUT cells comprising:
   a first group of CMUT cells each having a membrane comprising a first layer stack; and
   a second group of CMUT cells each having membrane comprising a second layer stack, the second layer stack including a layer of a material having a higher density than any of the layers in the first layer stack,
   wherein the membranes of the first group of CMUT cells have a first spring constant and the membranes of the second group of CMUT cells have a second spring constant that is no more than 20% different to the first spring constant, and
   wherein the plurality of CMUT cells are arranged in a staggered array comprising:
      a first column of spaced CMUT cells on at least one silicon island;
      a second column of spaced CMUT cells on at least one further silicon island, the second column being staggered in alignment with the first column such that cells of the second column are partially located in spaces between successive cells of the first column, the first column and the second column being spaced apart by a gap; and
      a flexible foil retaining the respective silicon islands, the flexible foil comprising conductive interconnects.

2. The transducer array of claim 1, wherein the second spring constant is no more than 10% different to the first spring constant.

3. The transducer array of claim 1, wherein:
   the first layer stack comprises a layer of a dielectric material to a first thickness; and
   the second layer stack comprises a layer of the dielectric material to a second thickness that is smaller than the first thickness; or
   the second layer stack comprises a layer of the dielectric material to the same thickness as the first layer stack and an additional layer comprising the layer of the material having a higher density than any of the layers in the first layer stack.

4. The transducer array of claim 1, comprising a plurality of transducer elements, each transducer element comprising at least one CMUT cell of the first group and at least one CMUT cell of the second group, wherein each CMUT cell of a transducer element of the plurality of transducer elements is configured to be controlled in the collapsed operation mode based with a same bias voltage.

5. The transducer array of claim 1, wherein the CMUT cells of the first group each have a first diameter and the CMUT cells of the second group each have a second diameter that is different to the first diameter.

6. The transducer array of claim 1, wherein the layer of a material having a higher density than any of the layers in the first layer stack has a density in excess of 7 g/cm$^3$, preferably a density in excess of 10 g/cm$^3$ and a Young's modulus of less than 200 GPa, preferably a Young's modulus of less than 100 GPa.

7. The transducer array of claim 1, wherein the layer of a material having a higher density than any of the layers in the first layer stack is a metal layer or metal alloy layer, preferably wherein the metal layer is a gold layer or a platinum layer.

8. The transducer array of claim 1, wherein the layer of a material having a higher density than any of the layers in the first layer stack is a patterned layer.

9. The transducer array of claim 1, wherein the first group of CMUT cells and the second group of CMUT cells are each arranged at a constant pitch in the staggered array.

10. The transducer array of claim 1, wherein:
    the first column of spaced CMUT cells is located on a first silicon island having opposing meandering edges, each edge meandering outwardly around one of the CMUT cells and meandering inwardly into a space between the CMUT cells;
    the second column of spaced CMUT cells is located on a second silicon island having opposing meandering edges, each edge meandering outwardly around one of the CMUT cells and meandering inwardly into a space between the CMUT cells; and
    the first silicon island is arranged adjacent to the second silicon island such that an outwardly meandering edge portion of the first silicon island slots into an inwardly meandering edge portion of the second silicon island.

11. The transducer array of claim 1, wherein:
    the first group of CMUT cells is configured to exhibit a first resonance frequency in the collapsed operation mode,
    the second group of CMUT cells is configured to exhibit a different, second resonance frequency in the collapsed operation mode,
    the first group of CMUT cells and the second group of CMUT cells are configured to be controlled in the collapsed operation mode with a same bias voltage, and
    the first group of CMUT cells and the second group of CMUT cells exhibit the different first and second resonance frequencies while being controlled in the collapsed operation mode with the same bias voltage.

12. A system comprising:
    a transducer array comprising plurality of CMUT cells suitable for a collapsed operation mode, each CMUT cell comprising a first electrode supported by a substrate and a second electrode supported by a membrane suspended over a cavity between the first electrode and the second electrode, the plurality of CMUT cells comprising:
       a first group of CMUT cells each having a membrane comprising a first layer stack; and
       a second group of CMUT cells each having membrane comprising a second layer stack, the second layer stack including a layer of a material having a higher density than any of the layers in the first layer stack, and
wherein the membranes of the first group of CMUT cells have a first spring constant and the membranes of the second group of CMUT cells have a second spring constant that is no more than 20% different to the first spring constant; and a controller configured to control the transducer array, wherein the plurality of CMUT cells are arranged in a staggered array comprising:

a first column of spaced CMUT cells on at least one silicon island;

a second column of spaced CMUT cells on at least one further silicon island, the second column being staggered in alignment with the first column such that cells of the second column are partially located in spaces between successive cells of the first column, the first column and the second column being spaced apart by a gap; and a flexible foil retaining the respective silicon islands, the flexible foil comprising conductive interconnects.

13. The system of claim 12, further comprising a power supply adapted to operate the CMUT cells in a collapse mode during at least one of an ultrasound transmission mode and an ultrasound reception mode.

14. The system of claim 12, wherein the transducer array is included in a probe.

* * * * *